United States Patent
Raghavan et al.

(10) Patent No.: US 11,639,500 B2
(45) Date of Patent: May 2, 2023

(54) METHOD OF RESIDUE PROXIMITY INFORMATION AND PROTEIN MODEL DISCRIMINATION USING SATURATION-SUPPRESSOR MUTAGENESIS

(71) Applicant: Indian Institute of Science, Bangalore (IN)

(72) Inventors: Varadarajan Raghavan, Bangalore (IN); Anusmita Sahoo, Bangalore (IN); Shruti Khare, Bangalore (IN); Pankaj Jain, Bangalore (IN); Shahbaz Ahmed, Bangalore (IN); Kritika Gupta, Bangalore (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 1371 days.

(21) Appl. No.: 15/779,800

(22) PCT Filed: Nov. 18, 2016

(86) PCT No.: PCT/IN2016/050413
§ 371 (c)(1),
(2) Date: May 29, 2018

(87) PCT Pub. No.: WO2017/094024
PCT Pub. Date: Jun. 8, 2017

(65) Prior Publication Data
US 2020/0299676 A1 Sep. 24, 2020

(30) Foreign Application Priority Data

Dec. 1, 2015 (IN) .......................... 6466/CHE/2015

(51) Int. Cl.
*C12N 15/10* (2006.01)
*G16B 15/00* (2019.01)
*G16B 20/00* (2019.01)

(52) U.S. Cl.
CPC ....... *C12N 15/1058* (2013.01); *C12N 15/102* (2013.01); *G16B 15/00* (2019.02); *G16B 20/00* (2019.02); *C07K 2299/00* (2013.01); *C12Y 207/0103* (2013.01)

(58) Field of Classification Search
None
See application file for complete search history.

(56) References Cited

PUBLICATIONS

Bajaj et al., "Structural Correlates of the Temperature Sensitive Phenotype Derived from Saturation Mutagenesis Studies of CcdB", Biochemistry, 2008, pp. 12964-12973, vol. 47.
International Search Report and Written Opinion for PCT/IN2016/050413 dated Apr. 17, 2017.
Jain et al., "A Rapid, Efficient, and Economical Inverse Polymerase Chain Reaction-Based Method for Generating a Site Saturation Mutant Library," Analytical Biochemistry, 2014, pp. 90-98, vol. 449.
Sahoo et al., "Residue Proximity Information and Protein Model Discrimination Using Saturation-Suppressor Mutagenesis," eLife, 2015, pp. 1-29, vol. 4.
Tripathi et al., "Residue Specific Contributions to Stability and Activity Inferred from Saturation Mutagenesis and Deep Sequencing," Current Opinion in Structural Biology, 2014, pp. 63-71, vol. 24.

*Primary Examiner* — Suzanne M Noakes
(74) *Attorney, Agent, or Firm* — Thompson Coburn LLP; William A. Holtz

(57) ABSTRACT

The present disclosure relates to a method of protein structure and amino acid residue interaction prediction based on saturation suppressor mutagenesis screening of a protein of interest. The method of the instant disclosure can be adapted for multi-protein complexes, and is useful where crystal structure of a protein of interest is not available.

9 Claims, 14 Drawing Sheets
Specification includes a Sequence Listing.

```
                            SEQUENCE LISTING

<160> NUMBER OF SEQ ID NOS: 2

<210> SEQ ID NO 1
<211> LENGTH: 101
<212> TYPE: PRT
<213> ORGANISM: artificial sequence
<220> FEATURE:
<223> OTHER INFORMATION: CcdB protein sequence

<400> SEQUENCE: 1

Met Gln Phe Lys Val Tyr Thr Tyr Lys Arg Glu Ser Arg Tyr Arg Leu
1               5                   10                  15

Phe Val Asp Val Gln Ser Asp Ile Ile Asp Thr Pro Gly Arg Arg Met
                20                  25                  30

Val Ile Pro Leu Ala Ser Ala Arg Leu Leu Ser Asp Lys Val Ser Arg
            35                  40                  45

Glu Leu Tyr Pro Val Val His Ile Gly Asp Glu Ser Trp Arg Met Met
        50                  55                  60

Thr Thr Asp Met Ala Ser Val Pro Val Ser Val Ile Gly Glu Glu Val
65                  70                  75                  80

Ala Asp Leu Ser His Arg Glu Asn Asp Ile Lys Asn Ala Ile Asn Leu
                85                  90                  95

Met Phe Trp Gly Ile
            100

<210> SEQ ID NO 2
<211> LENGTH: 121
<212> TYPE: PRT
<213> ORGANISM: artificial sequence
<220> FEATURE:
<223> OTHER INFORMATION: DgkA protein

<400> SEQUENCE: 2

Ala Asn Asn Thr Thr Gly Phe Thr Arg Ile Ile Lys Ala Ala Gly Tyr
1               5                   10                  15

Ser Trp Lys Gly Leu Arg Ala Ala Trp Ile Asn Glu Ala Ala Phe Arg
                20                  25                  30

Gln Glu Gly Val Ala Val Leu Leu Ala Val Val Ile Ala Ala Trp Leu
            35                  40                  45

Asp Val Asp Ala Ile Thr Arg Val Leu Leu Ile Ser Ser Val Met Leu
        50                  55                  60

Val Met Ile Val Glu Ile Leu Asn Ser Ala Ile Glu Ala Val Val Asp
65                  70                  75                  80

Arg Ile Gly Ser Glu Tyr His Glu Leu Ser Gly Arg Ala Lys Asp Met
                85                  90                  95

Gly Ser Ala Ala Val Leu Ile Ala Ile Ile Val Ala Val Ile Thr Trp
            100                 105                 110

Ala Ile Leu Leu Trp Ser His Phe Gly
        115                 120
```

METHOD OF RESIDUE PROXIMITY INFORMATION AND PROTEIN MODEL DISCRIMINATION USING SATURATION-SUPPRESSOR MUTAGENESIS

CROSS-REFERENCE TO RELATED APPLICATIONS

This patent application is a U.S. National Stage application under 35 U.S.C. § 371 of international application PCT/IN2016/050413, filed Nov. 18, 2016, which claims foreign priority to Indian application number 6466/CHE/2015, filed Dec. 1, 2015, both of which are incorporated herein in their entireties.

REFERENCE TO SEQUENCE LISTING SUBMITTED ELECTRONICALLY

The content of the electronically submitted sequence listing in ASCII text file (Name PD018240US-NP, SEQ LIST.txt; Size: 2,347 bytes; and Date of Creation: May 29, 2018) filed with the application is incorporated herein by reference in its entirety.

FIELD OF INVENTION

The present disclosure relates to the field of protein structure prediction based on saturation mutagenesis.

BACKGROUND OF THE INVENTION

Deducing the native conformation of a protein provides insight into its biological function. X-Ray crystallography and NMR are the major techniques used to accomplish this at atomic resolution. However, these require soluble purified protein at high concentration. In few cases (Garbuzynskiy, Melnik et al. 2005), the structures solved by the above two methods do not agree with each other, for various reasons. In many cases, the folded conformation is believed to be at a global free energy minimum (Anfinsen 1973). This can be used as a guide to either deduce the structure (Havel, Crippen et al. 1979) or fold a protein in-silico (Pande, Baker et al. 2003; Das and Baker 2008; Das, Andre et al. 2009).

The structural and functional integrity of a protein requires maintenance of specific interactions during the course of evolution. Evolution allows either conservation of these interacting pairs of residues or mutation at interacting positions in a correlated manner (Godzik and Sander 1989; Melero, Ollikainen et al. 2014). The fitness cost of most amino acid substitutions depends on the genetic context in which they occur. Substitutions beneficial in one background can be detrimental in a different background (Breen, Kemena et al. 2012; Shah, McCandlish et al. 2015). Interestingly, some sites are conserved not because a given amino acid is functionally irreplaceable, but rather because the right context is not available for its evolution (Wellner, Raitses Gurevich et al. 2013). This provides further evidence of correlation amongst mutations, i.e., epistatic interactions. Correlated substitutions have been experimentally identified in attempts to screen second-site suppressors which restore either stability, packing or functional defects of an inactive mutation (Hecht and Sauer 1985; Pakula and Sauer 1989; Machingo, Mazourek et al. 2001; Sideraki, Huang et al. 2001; Araya, Fowler et al. 2012). Correlated mutations have also been employed to identify protein interaction sites (Melamed, Young et al. 2015). Positive epistasis, where the fitness of two deleterious mutations in combination is higher than expected from the fitness of the individual mutants, is relatively rare. In an analysis of more than 1000 double mutants of HSP90, all eighteen examples of positive epistasis involved at least one mutation at an exposed position in the structure (Bank, Hietpas et al. 2015). Two other recent studies have examined a large number of second-site suppressors for RRM2 domain of the yeast poly(A)-binding protein (Pab1) and IgG-binding domain of protein G (GB1) respectively (Melamed, Young et al. 2013; Olson, Wu et al. 2014). In the present work, we carried out exhaustive screens for second-site suppressors of five inactive mutants of CcdB. In this study, though a small number of compensatory mutations were identified, in some cases these were ascertained to be spatially proximal while in others they were distal from the site of the original inactive mutation. High-throughput, exhaustive application of this approach combined with ways to disentangle proximal from distal suppressors would be a useful way to identify a substantial number of distance constraints (25-40% of true contacts) which can be used for protein structure prediction (Marks, Colwell et al. 2011). Evolutionary information contained in multiple homologous sequences of a protein has been decoded by various statistical approaches to identify correlated mutations (Gobel, Sander et al. 1994). Progressive improvement in this area has resulted in more accurate strategies which include use of a Bayesian network model (Burger and van Nimwegen 2010), maximum entropy in DCA (Morcos, Pagnani et al. 2011), sparse inverse covariance estimation in PSICOV (Jones, Buchan et al. 2012) and a pseudo-likelihood based approach in GREMLIN (Kamisetty, Ovchinnikov et al. 2013) to predict residue-residue contacts to computationally build protein 3D structures (Marks, Colwell et al. 2011; Nugent and Jones 2012; Sulkowska, Morcos et al. 2012; Ovchinnikov, Kamisetty et al. 2014). A sparse network of coevolving residues of a protein constraining its structure, specificity and function has been examined by statistical coupling analysis of evolutionarily rich sequence data in protein families (Halabi, Rivoire et al. 2009). Though these methods have great promise in the area of macromolecular structure determination, the fidelity of the predictions is questionable for candidates with small protein families, which have a size less than five times the length of the protein in case of GREMLIN (Kamisetty, Ovchinnikov et al. 2013) or less than 1,000 for some of the other methods.

Controller of Cell Division or Death B (CcdB) has few (~350) homologs in its protein family. This is <5L, where L=101 (number of residues in the protein chain). Using CcdB as a test system we describe experimental methodology to comprehensively identify spatially proximate residues by saturation suppressor analysis (FIG. 1), and its subsequent use in protein model discrimination and structure prediction. CcdB is the toxin component of the *Escherichia coli* CcdA-CcdB antitoxin-toxin system. It is a globular, dimeric protein with 101 residues per protomer, involved in maintenance of F plasmid in cells by a mechanism involving its binding to and poisoning of DNA Gyrase (Dao-Thi, Van Melderen et al. 2005).

Diacylglycerol kinase A (DgkA) is a homotrimeric integral transmembrane protein (121 residues per protomer) in *E. coli*, catalyzing the phosphorylation of diacylglycerol to phosphatidic acid. Gram-negative bacteria use this reaction product to shuttle water-soluble components to membrane-derived oligosaccharide and lipopolysaccharide in their cell envelope (Van Horn and Sanders 2012). The protein is captured in two distinct conformations by X-Ray crystallography (PDB id 3ZE5 (Li, Lyons et al. 2013)) and NMR (PDB id 2KDC (Van Horn, Kim et al. 2009)) respectively. The two structures are significantly different from each other, with 'domain swapping' being the key feature of the NMR model. Each structure is characterized by several unique residue contacts. It is important to identify whether one or both these structures are present in-vivo.

SUMMARY OF THE INVENTION

In an aspect of the present disclosure, there is provided a method for identifying functionally interacting amino acid residues in a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which decreases the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, wherein the two substituted amino acids in each variant of the said third subpopulation are indicative that the two amino acids at corresponding positions in wild-type said protein of interest are functionally interacting.

In an aspect of the present disclosure, there is provided a method for identifying suppressors of single amino acid mutants in a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, wherein the two substituted amino acids in each variant of said third subpopulation are indicative that the substituted amino acid of variant member of first library is a suppressor of the substituted amino acid of first subpopulation.

In an aspect of the present disclosure, there is provided a method for predicting the structure of a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation; and (f) generating a predictive structure of said protein of interest based on identification of pairs of interacting amino acid residues in each variant of the third subpopulation.

In an aspect of the present disclosure, there is provided a method for identification of amino acid residues and residue positions which modulate thermal stability of a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, and in each variant of the third subpopulation, the substituted amino acid of variant member of first library is a distal suppressor, said distal suppressor is able to suppress the altered activity of more than one variant comprising a single substituted amino acid as identified in the said first subpopulation, wherein the said variants of the first subpopulation have amino acid substitutions in different residue positions, and said amino acid substitutions in different residues do not suppress each other, wherein said mutation as identified from each variant of said first library is an amino acid which at the particular residue position modulates thermal stability of said protein of interest.

In an aspect of the present disclosure, there is provided a library of single mutation variants of a protein of interest, wherein said each variant contains an amino acid substitution at a single residue position, and at least 70% of each possible amino acid substitution at each residue position of said protein of interest is represented in said library.

In an aspect of the present disclosure, there is provided a library of single mutation variants of a protein of interest, wherein each variant exhibits decreased activity compared to wild-type protein of interest activity.

In an aspect of the present disclosure, there is provided a library of two mutation variants of a protein of interest, wherein said library is obtained by introducing at least five mutations at different residue positions singly in to each variant of the library comprising single mutation variants of a protein of interest, wherein each variant exhibits decreased activity compared to wild-type protein of interest activity.

In an aspect of the present disclosure, there is provided a library of single mutation variants of a protein of interest, wherein said each variant contains an amino acid substitution at a single residue position, and at least 70% of each possible amino acid substitution at each residue position of said protein of interest is represented in said library, for use in identifying functionally interacting amino acid residues in a protein of interest, identifying suppressors of single amino acid mutants in a protein of interest, for predicting the structure of a protein of interest, or identification of amino acid residues and residue positions which modulate thermal stability of a protein of interest.

In an aspect of the present disclosure, there is provided a library of single mutation variants of a protein of interest, wherein each variant exhibits decreased activity compared to wild-type protein of interest activity, for use in identifying functionally interacting amino acid residues in a protein of interest, identifying suppressors of single amino acid mutants in a protein of interest, for predicting the structure of a protein of interest, or identification of amino acid residues and residue positions which modulate thermal stability of a protein of interest.

In an aspect of the present disclosure, there is provided a library of two mutation variants of a protein of interest, wherein said library is obtained by introducing at least five mutations at different residue positions singly in to each variant of a library of single mutation variants of a protein of interest, wherein each variant exhibits decreased activity compared to wild-type protein of interest activity, for use in identifying functionally interacting amino acid residues in a protein of interest, identifying suppressors of single amino acid mutants in a protein of interest, for predicting the structure of a protein of interest, or identification of amino acid residues and residue positions which modulate thermal stability of a protein of interest.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DESCRIPTION OF TABLES

Figure 1:
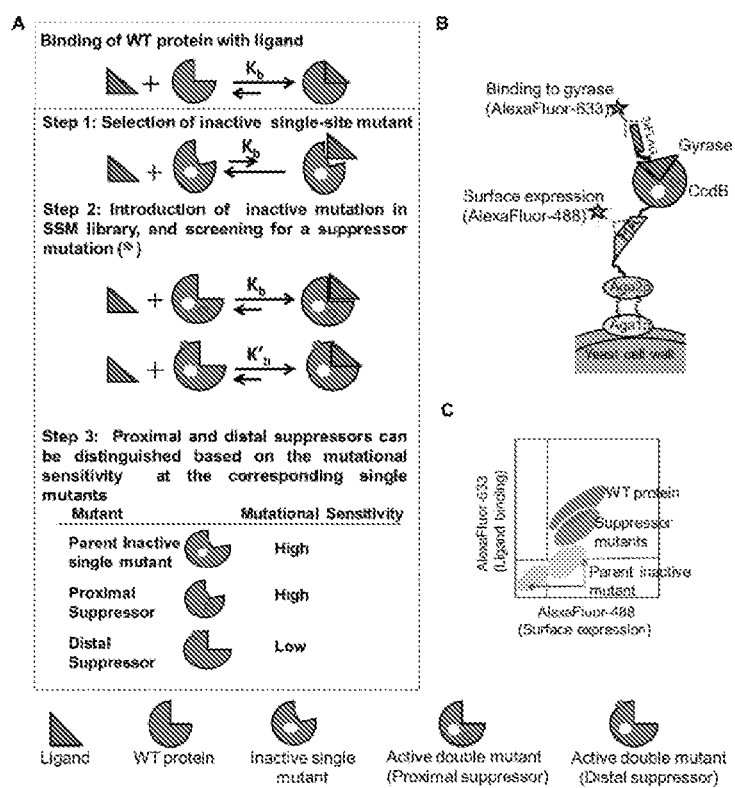
FIG. 1 depicts the strategy adopted to determine proximal residue pairs, in accordance with an embodiment of the present disclosure.

Table 1 depicts the summary of sort details for different libraries of CcdB.

Table 2 depicts that experimentally determined (PIM, suppressor) pairs for CcdB occur at both spatially proximate and distal residues.

Table 3 depicts the relative expression, binding and stabilities of PIMs and their suppressors in the case of CcdB.

Table 4 depicts the experimentally determined (PIM, Suppressor) pairs for DgkA are spatially close only in the corresponding crystal structure.

Table 5 depicts the sidechain-sidechain centroid distances and shortest distances between the listed residue pairs for putative differential contacts between DgkA X-ray and NMR structures (experimentally observed (PIM,suppressor) pairs are indicated in bold).

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "functionally interacting amino acid residues" refers to amino acid residues in a protein or protein complex which are evolutionary linked.

The term "altered activity" refers to change in activity of a said protein with respect to wild type/native activity level. The altered activity may be increase or decrease in activity with regard to wild type/native activity. For the purposes of the instant disclosure, the altered activity here is decrease in activity compared to native/wild type activity.

The term "distal suppressor" used in the instant disclosure refers to an amino acid residue which is able to suppress the altered activity of at least two variants of a protein of interest, wherein in each variant there is a single amino acid mutation. Distal suppressors are likely to be present on the surface of said protein. The term "distal suppressor" can also be interchangeably used with the term "global suppressor".

The term "population" refers to all variants of a protein obtained from a mutagenesis screen.

The term "subpopulation of" refers to a subset of a population of variants of a protein obtained from a mutagenesis screen.

The term "proximal suppressor" used in the instant disclosure refers to an amino acid residue which is able to suppress the altered activity of a single variant of a protein of interest, wherein in each variant there is a single amino acid mutation.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

Sequences:

SEQ ID NO: 1 depicts the amino acid sequence of CcdB.
SEQ ID NO: 2 depicts the amino acid sequence of DgkA.

In an embodiment of the present disclosure, there is provided a method for identifying functionally interacting amino acid residues in a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which decreases the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, wherein the two substituted amino acids in each variant of the said third subpopulation are indicative that the two amino acids at corresponding positions in wild-type said protein of interest are functionally interacting.

In an embodiment of the present disclosure, there is provided a method for identifying functionally interacting amino acid residues in a protein of interest as described herein, wherein in step (a) at least 71%, 72%, 73%, 74%, 75%, 76%, 77%, 78%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of each possible amino acid substitutions at each residue position of said protein of interest is represented in said first library.

In an embodiment of the present disclosure, there is provided a method for identifying functionally interacting amino acid residues in a protein of interest as described herein, wherein said protein of interest is a single protein.

In an embodiment of the present disclosure, there is provided a method for identifying functionally interacting amino acid residues in a protein of interest as described herein, wherein said protein of interest is a multi-protein complex.

In an embodiment of the present disclosure, there is provided a method for identifying functionally interacting amino acid residues in a protein of interest as described herein, wherein said protein is an antibody-antigen complex.

In an embodiment of the present disclosure, there is provided a method for identifying functionally interacting amino acid residues in a protein of interest as described herein, wherein said protein is a receptor-ligand complex.

In an embodiment of the present disclosure, there is provided a method for identifying functionally interacting amino acid residues in a protein of interest as described herein, wherein said amino acid substitution is a naturally occurring amino acid.

In an embodiment of the present disclosure, there is provided a method for identifying functionally interacting amino acid residues in a protein of interest as described herein, wherein said amino acid substitution is a synthetic amino acid.

In an embodiment of the present disclosure, there is provided a method for identifying functionally interacting amino acid residues in a protein of interest as described herein, wherein in step (c) mutations at all the different residue positions from said first subpopulation are singly introduced in to each variant of the first library.

In an embodiment of the present disclosure, there is provided a method for identifying functionally interacting amino acid residues in a protein of interest as described herein, wherein in step (c) variants of the second library have two amino acid substitutions in said protein of interest.

In an embodiment of the present disclosure, there is provided a method for identifying functionally interacting amino acid residues in a protein of interest as described herein, wherein in step (c) variants of the second library have one amino acid substitutions in said protein of interest.

In an embodiment of the present disclosure, there is provided a method for identifying suppressors of single amino acid mutants in a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, wherein the two substituted amino acids in each variant of said third subpopulation are indicative that the substituted amino acid of variant member of first library is a suppressor of the substituted amino acid of first subpopulation.

In an embodiment of the present disclosure, there is provided a method for identifying suppressors of single amino acid mutants in a protein of interest as described herein, wherein in step (a) at least 71%, 72%, 73%, 74%, 75%, 76%, 77%, 78%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of each possible amino acid substitutions at each residue position of said protein of interest is represented in said first library.

In an embodiment of the present disclosure, there is provided a method for identifying suppressors of single amino acid mutants in a protein of interest as described herein, wherein in each variant of the third subpopulation, substituted amino acid of variant member of first library is a distal suppressor, said distal suppressor is able to suppress the altered activity of more than one variant comprising a single substituted amino acid as identified in the said first subpopulation, wherein the said variants of the first subpopulation have amino acid substitutions in different residue positions, and said amino acid substitutions in different residues do not suppress each other.

In an embodiment of the present disclosure, there is provided a method for identifying suppressors of single amino acid mutants in a protein of interest as described herein, wherein in each variant of the third subpopulation the substituted amino acid of variant member of first library is a proximal suppressor, wherein said proximal suppressor is able to suppress the altered activity of at least one variant comprising a single substituted amino acid as identified in the said first subpopulation.

In an embodiment of the present disclosure, there is provided a method for identifying suppressors of single amino acid mutants in a protein of interest as described herein, wherein said protein of interest is a single protein.

In an embodiment of the present disclosure, there is provided a method for identifying suppressors of single amino acid mutants in a protein of interest as described herein, wherein said protein of interest is a multi-protein complex.

In an embodiment of the present disclosure, there is provided a method for identifying suppressors of single amino acid mutants in a protein of interest as described herein, wherein said protein is an antibody-antigen complex.

In an embodiment of the present disclosure, there is provided a method for identifying suppressors of single amino acid mutants in a protein of interest as described herein, wherein said protein is a receptor-ligand complex.

In an embodiment of the present disclosure, there is provided a method for identifying suppressors of single amino acid mutants in a protein of interest as described herein, wherein said amino acid substitution is a naturally occurring amino acid.

In an embodiment of the present disclosure, there is provided a method for identifying suppressors of single amino acid mutants in a protein of interest as described herein, wherein said amino acid substitution is a synthetic amino acid.

In an embodiment of the present disclosure, there is provided a method for identifying suppressors of single amino acid mutants in a protein of interest as described herein, wherein in step (c) mutations at all the different residue positions from said first subpopulation are singly introduced in to each variant of the first library.

In an embodiment of the present disclosure, there is provided a method for identifying suppressors of single amino acid mutants in a protein of interest as described herein, wherein in step (c) variants of the second library have two amino acid substitutions in said protein of interest.

In an embodiment of the present disclosure, there is provided a method for identifying suppressors of single amino acid mutants in a protein of interest as described herein, wherein in step (c) variants of the second library have one amino acid substitutions in said protein of interest.

In an embodiment of the present disclosure, there is provided a method for predicting the structure of a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation; and (f) generating a predictive structure of said protein of interest based on identification of pairs of interacting amino acid residues in each variant of the third subpopulation.

In an embodiment of the present disclosure, there is provided a method for predicting the structure of a protein of interest as described herein, wherein in step (a) at least 71%, 72%, 73%, 74%, 75%, 76%, 77%, 78%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of each possible amino acid substitutions at each residue position of said protein of interest is represented in said first library.

In an embodiment of the present disclosure, there is provided a method for predicting the structure of a protein of interest as described herein, wherein said protein of interest is a single protein.

In an embodiment of the present disclosure, there is provided a method for predicting the structure of a protein of interest as described herein, wherein said protein of interest is a multi-protein complex.

In an embodiment of the present disclosure, there is provided a method for predicting the structure of a protein of interest as described herein, wherein said protein is an antibody-antigen complex.

In an embodiment of the present disclosure, there is provided a method for predicting the structure of a protein of interest as described herein, wherein said protein is a receptor-ligand complex.

In an embodiment of the present disclosure, there is provided a method for predicting the structure of a protein of interest as described herein, wherein said amino acid substitution is a naturally occurring amino acid.

In an embodiment of the present disclosure, there is provided a method for predicting the structure of a protein of interest as described herein, wherein said amino acid substitution is a synthetic amino acid.

In an embodiment of the present disclosure, there is provided a method for predicting the structure of a protein of interest as described herein, wherein in step (c) mutations at all the different residue positions from said first subpopulation are singly introduced in to each variant of the first library.

In an embodiment of the present disclosure, there is provided a method for predicting the structure of a protein of interest as described herein, wherein in step (c) variants of the second library have two amino acid substitutions in said protein of interest.

In an embodiment of the present disclosure, there is provided a method for predicting the structure of a protein of interest as described herein, wherein in step (c) variants of the second library have one amino acid substitutions in said protein of interest.

In an embodiment of the present disclosure, there is provided a method for identification of amino acid residues and residue positions which modulate thermal stability of a protein of interest, said method comprising: (a) obtaining a first library of single mutation variants of said protein of interest, wherein said each variant contains an amino acid substitution at a single residue position, and at least 70% of each possible amino acid substitution at each residue position of said protein of interest is represented in said first library; (b) identifying a first subpopulation of variants, wherein said first subpopulation comprises a population enriched in variants, each of which alters the activity of said protein of interest compared to wild-type levels; (c) introducing at least five mutations at different residue positions from said first subpopulation singly in to each variant of the first library to obtain a second library of variants having two or one amino acid substitution in said protein of interest; (d) identifying a second subpopulation from said second library, comprising variants, each of which has two amino acid substitutions; (e) identifying a third subpopulation, which is a subset of the said second subpopulation of said second library, wherein in each variant of said third subpopulation, the mutation as identified from each variant of said first library suppresses the altered activity of the variant of the first subpopulation, and in each variant of the third subpopulation, the substituted amino acid of variant member of first library is a distal suppressor, said distal suppressor is able to suppress the altered activity of more than one variant comprising a single substituted amino acid as identified in the said first subpopulation, wherein the said variants of the first subpopulation have amino acid substitutions in different residue positions, and said amino acid substitutions in different residues do not suppress each other, wherein said mutation as identified from each variant of said first library is an amino acid which at the particular residue position modulates thermal stability of said protein of interest.

In an embodiment of the present disclosure, there is provided a method for identification of amino acid residues and residue positions which modulate thermal stability of a protein of interest as described herein, wherein in step (a) at least 71%, 72%, 73%, 74%, 75%, 76%, 77%, 78%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of each possible amino acid substitutions at each residue position of said protein of interest is represented in said first library.

In an embodiment of the present disclosure, there is provided a method for identification of amino acid residues and residue positions which modulate thermal stability of a protein of interest as described herein, wherein said protein of interest is a single protein.

In an embodiment of the present disclosure, there is provided a method for identification of amino acid residues and residue positions which modulate thermal stability of a protein of interest as described herein, wherein said protein of interest is a multi-protein complex.

In an embodiment of the present disclosure, there is provided a method for identification of amino acid residues and residue positions which modulate thermal stability of a protein of interest as described herein, wherein said protein is an antibody-antigen complex.

In an embodiment of the present disclosure, there is provided a method for identification of amino acid residues and residue positions which modulate thermal stability of a protein of interest as described herein, wherein said protein is a receptor-ligand complex.

In an embodiment of the present disclosure, there is provided a method for identification of amino acid residues and residue positions which modulate thermal stability of a protein of interest as described herein, wherein said amino acid substitution is a naturally occurring amino acid.

In an embodiment of the present disclosure, there is provided a method for identification of amino acid residues and residue positions which modulate thermal stability of a protein of interest as described herein, wherein said amino acid substitution is a synthetic amino acid.

In an embodiment of the present disclosure, there is provided a method for identification of amino acid residues and residue positions which modulate thermal stability of a protein of interest as described herein, wherein in step (c) mutations at all the different residue positions from said first subpopulation are singly introduced in to each variant of the first library.

In an embodiment of the present disclosure, there is provided a method for identification of amino acid residues and residue positions which modulate thermal stability of a protein of interest as described herein, wherein in step (c) variants of the second library have two amino acid substitutions in said protein of interest.

In an embodiment of the present disclosure, there is provided a method for identification of amino acid residues and residue positions which modulate thermal stability of a protein of interest as described herein, wherein in step (c) variants of the second library have one amino acid substitutions in said protein of interest.

The following description below is purely for illustrative purposes in order for a person skilled in the art to appreciate the scope and extent of the claimed subject matter.

Hypothetical protein of "n amino acids, where n=5 (non-limiting example where said hypothetical protein is a single protein. Hypothetical protein which is a complex as described in the instant specification of varied amino acid length is contemplated and within the purview of a person skilled in the art)" amino acids of sequence n-4:n-3:n-2:n-1:n. In the first round of mutations, a library of single amino acid mutations are obtained, said library comprising of the following variants (* denotes residue position where amino acid has been substituted by any other natural or synthetic amino acid not present in the wild type protein at the particular position); (a) n-4*:n-3:n-2:n-1:n; (b) n-4:n-3*:n-2:n-1:n; (c) n-4:n-3:n-2*:n-1:n; (d) n-4:n-3:n-2:n-1*:n; (e) n-4:n-3:n-2:n-1:n*. Next, variants are identified which result in decrease in wild type level of protein activity (example (non-limiting): n-4*:n-3:n-2:n-1:n). Next, the n-4* is introduced into each of variants in the first library to obtain variants with amino acid substitutions at two different positions, namely, (a) n-4*:n-3*:n-2:n-1:n; n-4*:n-3:n-2*:n-1:n; n-4*:n-3:n-2:n-1*:n; and n-4*:n-3:n-2:n-1:n*. The said library of variants is screened for variants where the n-4* phenotype is suppressed by the corresponding 2$^{nd}$ mutation in the said variant (example (non-limiting): n-4*:n-3:n-2:n-1*:n. In this instance, it can be said that the amino acid at n-1 position is functionally interacting with the amino acid at n-4 position in said hypothetical protein. Based on suppression phenotype, further inference may be drawn regarding co-evolution of said pair(s) of functionally interacting amino acids. Suppressors can also be identified, along with amino acid residues and residue positions that may be involved in thermal tolerance of higher order protein structure. Based on the analysis, as described in detail in the instant disclosure, the suppressors may be termed as "proximal" or "distal/global" based on their ability to suppress the inactivating phenotype of one more amino acid substitutions. The information can also be used to predict the structure of the said hypothetical protein in the absence of availability of crystals for X-ray diffraction.

In an embodiment of the present disclosure, there is provided a method as described herein, wherein said protein of interest amino acid sequence is as set forth in SEQ ID NO: 1.

In an embodiment of the present disclosure, there is provided a method as described herein, wherein said protein of interest amino acid sequence is as set forth in SEQ ID NO: 2.

In an embodiment of the present disclosure, there is provided a library of single mutation variants of a protein of interest, wherein said each variant contains an amino acid substitution at a single residue position, and at least 70% of each possible amino acid substitution at each residue position of said protein of interest is represented in said library.

In an embodiment of the present disclosure, there is provided a library of single mutation variants of a protein of interest, wherein said each variant contains an amino acid substitution at a single residue position, and at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of each possible amino acid substitution at each residue position of said protein of interest is represented in said library.

In an embodiment of the present disclosure, there is provided a library of single mutation variants of a protein of interest, wherein each variant exhibits decreased activity compared to wild-type protein of interest activity.

In an embodiment of the present disclosure, there is provided a library of two mutation variants of a protein of interest, wherein said library is obtained by introducing at least five mutations at different residue positions singly in to each variant of a library comprising single mutation variants of a protein of interest, wherein each variant exhibits decreased activity compared to wild-type protein of interest activity.

In an embodiment of the present disclosure, there is provided a library of two mutation variants of a protein of interest, wherein said library is obtained by introducing five mutations at different residue positions singly in to each variant of a library comprising single mutation variants of a protein of interest, wherein each variant exhibits decreased activity compared to wild-type protein of interest activity.

In an embodiment of the present disclosure, there is provided a library as described herein, wherein said library is a yeast library.

In an embodiment of the present disclosure, there is provided a library as described herein, for use in identifying functionally interacting amino acid residues in a protein of interest.

In an embodiment of the present disclosure, there is provided a library as described herein, for use in identifying suppressors of single amino acid mutants in a protein of interest.

In an embodiment of the present disclosure, there is provided a library as described herein, for use in predicting the structure of a protein of interest.

In an embodiment of the present disclosure, there is provided a library as described herein, for use in identification of amino acid residues and residue positions which modulate thermal stability of a protein of interest.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Library Preparation and Isolation of Suppressor Mutants of CcdB

Figure 2:
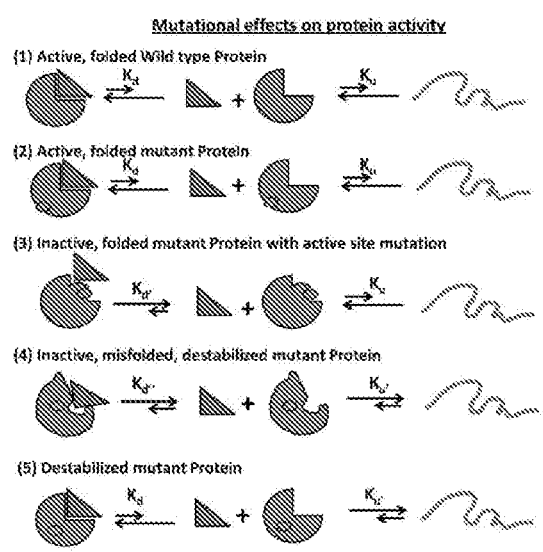
FIG. 2 depicts possible mechanisms for reduced activity of a mutant protein, in accordance with an embodiment of the present disclosure.
Figure 3:
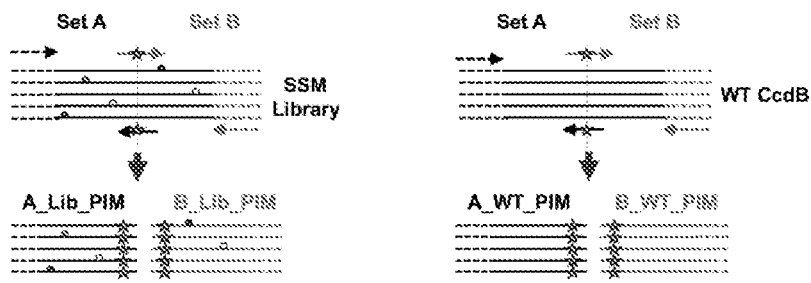
FIG. 3 depicts the strategy to introduce an inactive mutant into all members of a single-site saturation mutagenesis (SSM) library of a gene cloned in a yeast surface display (YSD) vector, in accordance with an embodiment of the present disclosure.
Figure 3:
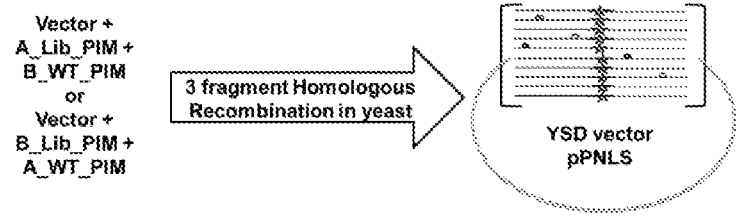

Relative activities of ~1430 single-site mutants of CcdB have been obtained previously from phenotypic screening and deep sequencing of an SSM library (Adkar, Tripathi et al. 2012). This data was analyzed to select five inactive mutants; V5F, V18W, V20F, L36A and L83S (hereafter referred to as parent inactive mutants (PIMs)) at non-active site residues. Both buried and active site residue positions possess high RankScores and high average mutational sensitivity ($MS_{seq}$) values for individual mutants. Active-site residues can be distinguished from buried ones based on the pattern of mutational sensitivity. Mutational sensitivity ($MS_{seq}$) scores were determined from the sequencing analysis of the single-site saturation library of CcdB and refer to the expression level at which partial loss of function mutants showed an active phenotype (methodology described in (Adkar, Tripathi et al. 2012)). At buried positions, typically most aliphatic substitutions are tolerated, Polar and charged residues are poorly tolerated at buried positions. In contrast, mutations to aliphatic residues are often poorly tolerated at active site residues (which are typically exposed), polar and charged residues are sometimes tolerated and also the average mutational tolerance is typically lower than that for buried residues. Mutational tolerance is the fraction of active mutants for each mutant amino acid. Based on the above criteria residues Q2, F3, Y6, S22, I24, N95, W99, G100 and I101 can be identified as putative active-site residues based solely on the mutational data (data not provided). Similar mutational patterns are seen for two other proteins for which extensive mutational data exist, the PDZ domain (PSD95$^{pdz3}$) (McLaughlin, Poelwijk et al. 2012) and the IgG-binding domain of protein G (GB1) (Olson, Wu et al. 2014). Recent work (Melamed, Young et al. 2015) suggests that saturation mutagenesis in combination with evolutionary conservation data can also be used to identify residues at interaction sites. In addition to differences in mutational sensitivity patterns, an important difference between active-site and buried-site mutations is that the former typically affect specific activity and not the level of properly folded protein, while the latter primarily affect the level of properly folded protein (Bajaj, Dewan et al. 2008). Thus measurements of protein levels, and possibly sensitivity of mutant activity to chaperone overexpression (Tokuriki and Tawfik 2009), can also be used to distinguish between active-site and buried-site mutants. The average hydrophobicity and hydrophobic moment (Varadaraj an, Nagarajaram et al. 1996) are supplementary parameters that can help distinguish between exposed, active-site and buried-site residues. Mutations at the selected non active-site positions perturb activity by reducing the amount of functional, folded protein in vivo (FIG. 2) (Bajaj, Dewan et al. 2008). PIMs were chosen so as to include different kinds of mutations, namely large→small, small→large and hydrophobic→polar. In order to identify residues which can compensate for the PIM, the selected inactive mutations were individually introduced into the SSM library. The resulting double mutant saturation-suppressor libraries were cloned into a yeast surface display (YSD) vector (pPNLS) by three fragment recombination in Saccharomyces cerevisiae (FIG. 3).

Figure 4:
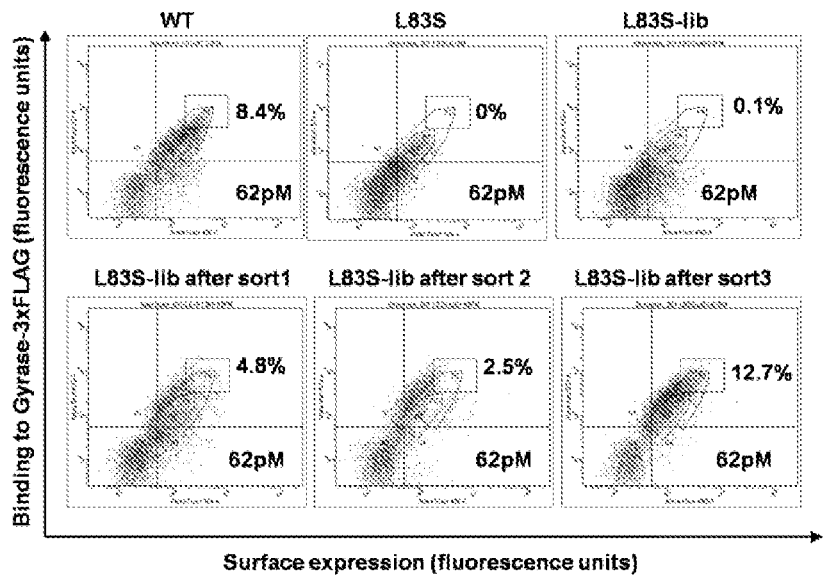
FIG. 4 depicts the enrichment of second-site suppressor population for L83S CcdB inactive mutant following multiple rounds of FACS, in accordance with an embodiment of the present disclosure.

Recombination yielded ~10$^5$ transformants for each library. YSD and fluorescence activated cell sorting (FACS) were used as screening tools to isolate populations exhibiting (i) enhanced binding to the ligand DNA Gyrase, and (ii) increased surface expression relative to the corresponding PIM. The ligand concentration was decreased in subsequent rounds of sorting to increase the stringency in selection of true suppressors (Table 1). The methodology used to generate the library along with the use of very low (pg) amount of template DNA for PCR was effective in introducing the PIM into all members of the SSM library. This is important as the presence of even a small fraction of WT residue at the position of the PIM will rapidly lead to its selection, resulting in a high amount of false positive data. Following multiple rounds of sorting (typically 3-4), over 10% of the population was shown to bind significantly better than the PIM. Data for the L83S mutant library is shown (FIG. 4). At this stage, 96 individual clones for each library were sequenced by Sanger sequencing to identify 1-3 potential suppressors for each PIM (Table 2).

Example 2

Discrimination Between Proximal and Distal Suppressors

For a pair of residues in contact, it is likely that a destabilizing substitution at one residue can be suppressed by a complementary substitution at the other residue. For example, a cavity formed by a large→small substitution of a residue may be compensated by a small→large substitution of the partner residue in contact with it. Consequently, while each of the individual mutations will be destabilizing in the WT background, the pair will have increased stability and activity relative to their corresponding single mutants. However, suppressors can be either spatially proximal or distal from the site of the original inactive mutation. In contrast to proximal suppressors, distal suppressors will typically be on the surface of protein (Bank, Hietpas et al. 2015) and hence the individual suppressor mutation is expected to be neutral in the WT background. Further, unlike proximal suppressors no complementarity relative to the PIM is expected for a distal suppressor. "RankScore", previously described (Adkar, Tripathi et al. 2012), is a parameter which scores a residue based on its average mutational sensitivity (in a single-mutant library) and correlates positively with residue depth (r=0.61) and negatively with mutational tolerance. The value for RankScore ranges between 1 and 100. For a given non active-site residue, a higher value of RankScore indicates that the residue is likely to be buried in the protein structure. All the PIMs were chosen such that they are non active-site and have a high RankScore. Hence, they are likely to be buried in the protein structure and in fact, are buried. It is therefore expected that positions at which local suppressors occur will also have high depth, high RankScores and high average mutational sensitivity in the SSM library (FIG. 1A). All the positions with low RankScores are exposed on the protein structure. Hence, suppressors with RankScore=1 were classified as distal suppressors (Table 2). A RankScore of 1 is a conservative cutoff for distal suppressors; probably a cutoff of five or ten would yield similar results. The RankScore cutoff of 25 which we have chosen for proximal suppressors, clearly identifies only buried residues with depth >5.5 Å. All these residues have accessibility <1.5%. In the present work we assume that distal suppressors will be global suppressors. Hence, the most reliable way to identify these would be to confirm that the same putative distal suppressor is able to suppress multiple PIMs, preferably PIMs which are not in contact with each other. The latter is likely to be true if neither PIM has a suppressor at the site of the other PIM. Using these criteria we can clearly infer that R10G, E11R, E11K and E11P are likely global suppressors.

Figure 5:
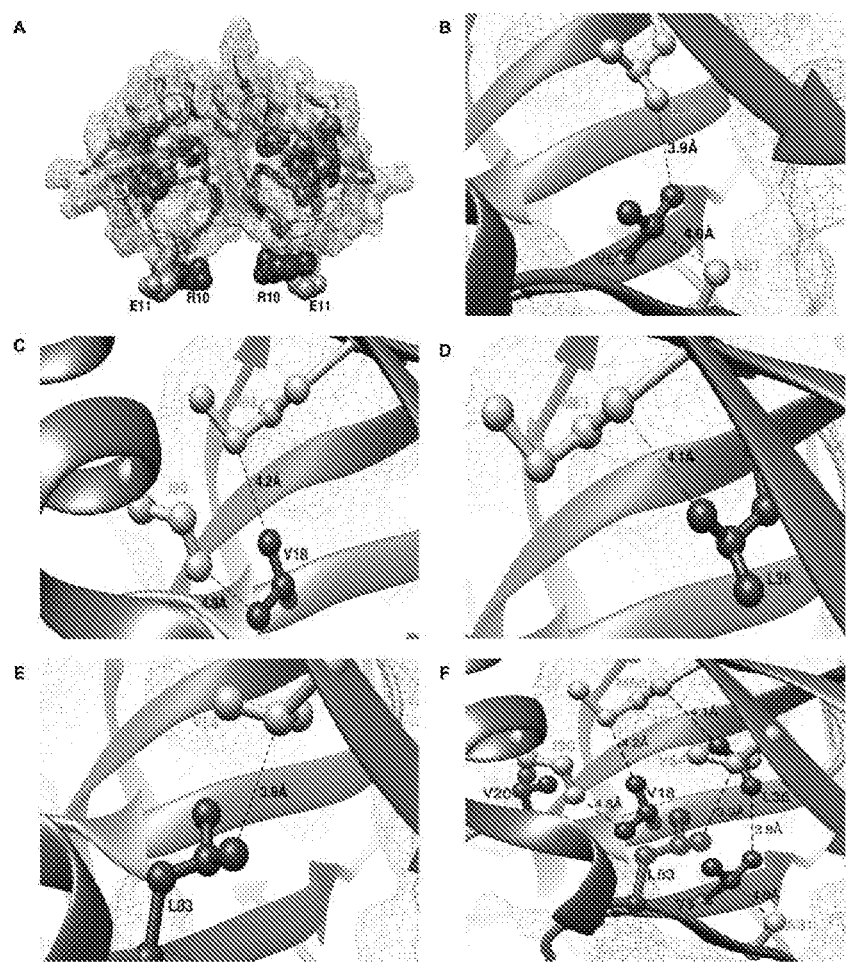
FIG. 5 depicts the experimentally obtained (PIM, suppressors) pairs mapped onto the crystal structure of CcdB, in accordance with an embodiment of the present disclosure.

The PCR strategy adopted (FIG. 3) to construct the second-site suppressor mutagenesis library for screening suppressors against the PIMs of CcdB was designed to generate (i) 50% double mutants with each member containing the PIM and a single mutant, and (ii) 50% PIMs. Sequencing data obtained was analyzed to identify proximal and distal suppressors (as discussed above). We largely obtained double mutants containing the PIM and a suppressor, and a small fraction of the triple mutant (V5F/L36M/A81G) (Table 2). Occurrence of the triple mutant was due to selection and enrichment of an additional mutation introduced into the double mutant library likely due to PCR based errors. The selected triple mutant contained the PIM V5F and two proximal suppressors (L36M and A81G). Six residue pairs were identified which contained the PIM and a proximal suppressor (Table 2). The shortest distance between corresponding residue pairs in the structure of WT CcdB was 2.8-4.8 Å (PDB id: 3VUB (Loris, Dao-Thi et al. 1999), Table 2, FIG. 5B-E). This validated the methodology described above. Two residues, R10 and E11 (in the pairs L36A/R10G, L36A/E11P, V20F/E11R and V20F/E11K) were identified as distal suppressors based on their low RankScore values in the SSM library. The shortest distances between L36-R10 and V20-E11 are 11.6 Å and 18.4 Å respectively. As expected, the local suppressors are clustered together in the protein interior while the distal ones are present on an exposed loop region (FIG. 5A).

Example 3

Protein Stabilization by the Suppressor Mutants

Figure 6:
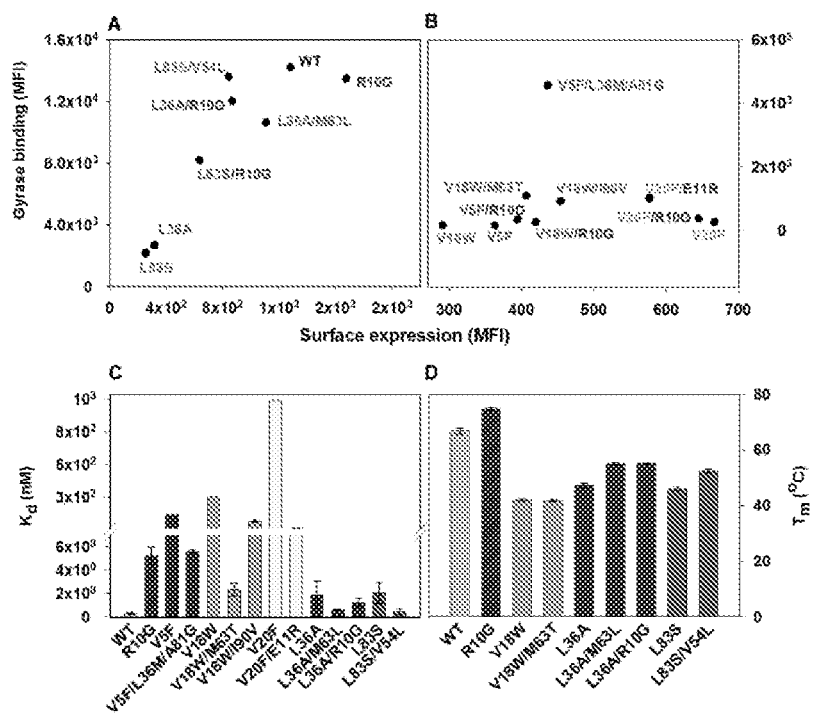
FIG. 6 depicts the restoration of defects in CcdB PIMs by suppressors, in accordance with an embodiment of the present disclosure.
Figure 7:
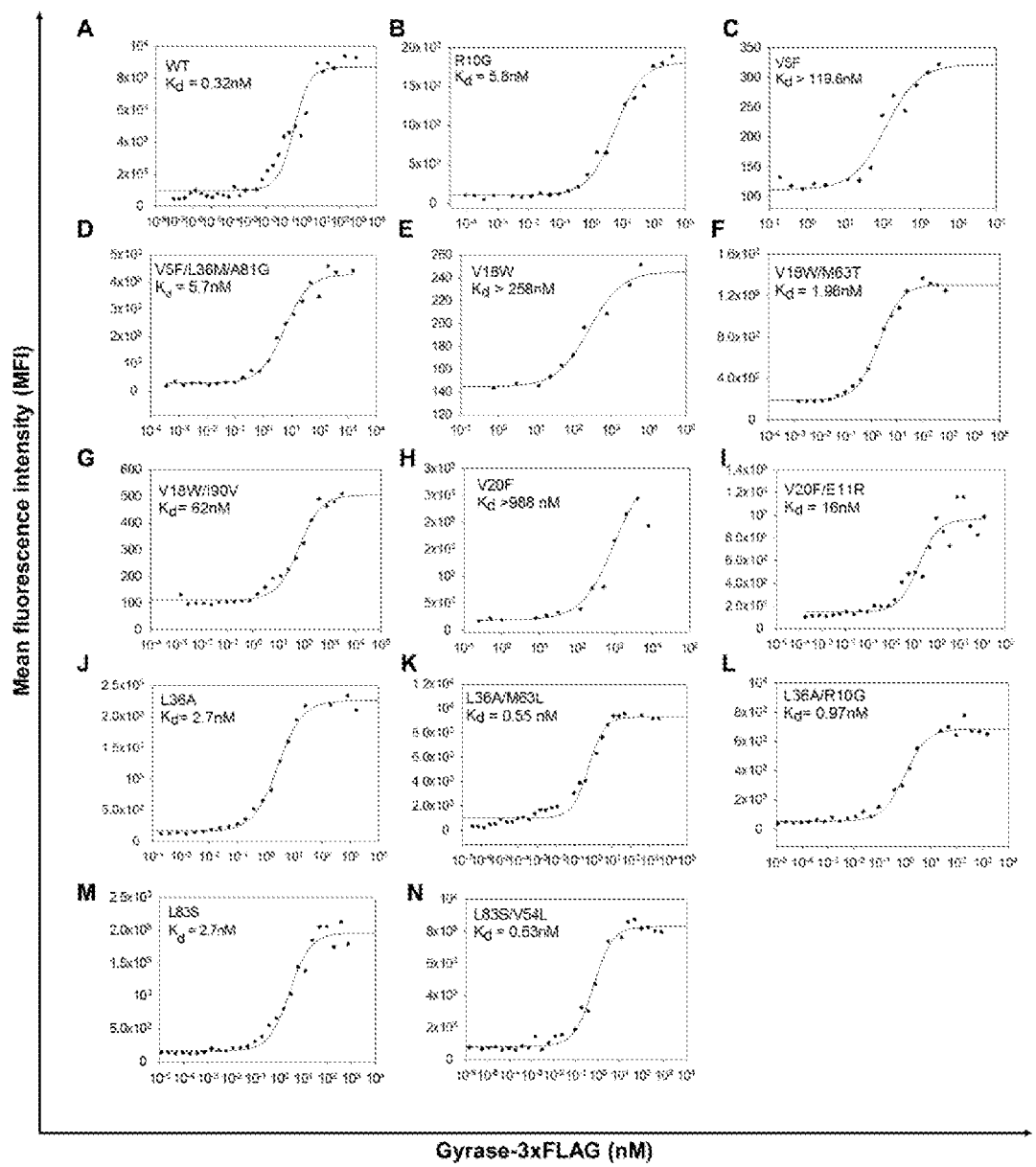
FIG. 7 depicts the YSD titrations of PIMs pairs to determine $K_d$ between CcdB displayed on the yeast surface and purified gyrase, in accordance with an embodiment of the present disclosure.

Identified CcdB suppressors individually conferred improved binding and thermal stability over the corresponding PIMs (FIG. 6, 7, 8, Table 3). An increased affinity for DNA Gyrase for the (PIM, suppressor) pair relative to the PIM alone was observed in all cases except for (L36A, M63L) and (L36A, R10G) pairs (FIG. 6C), which exhibited similar affinity towards Gyrase as the PIM L36A. However, the (PIM, suppressor) pairs showed higher thermal stability ($T_m$(L36A, M63L)=55±0.8° C., $T_m$(L36A, R10G)= 55.1±0.4° C., $T_m$(L36A)=47.1±0.3° C.) and increased surface expression (FIG. 6A, D). Surface expression levels of proteins displayed on the yeast surface have previously been found to correlate with the protein's stability (Shusta, Kieke et al. 1999). Increased surface expression was observed for all (PIM, suppressor) pairs (including the distal suppressor (L36A, R10G) pair) relative to the PIM, except for the (V20F, E11R) pair (FIG. 6A, B). This distal suppressor pair exhibited slightly lower expression than its PIM, V20F, but displayed enhanced activity in terms of its binding to Gyrase (FIG. 6B, C).

R10G is a distal suppressor. The ability of the R10G mutation to suppress defects at other positions was examined by constructing the corresponding double mutants. Increased surface expression of R10G paired with each of V5F, V18W, L36A and L83S was seen relative to the individual PIMs (FIG. 6A, B). This demonstrates that R10G likely acts as a global suppressor. E11 suppresses activity of two PIMs, L36A and V20F (L36A/E11P, V20F/E11R, V20F/E11K) and is anticipated to play a role similar to R10G. Both R10 and E11 are present on a loop region in the structure (FIG. 5A).

Example 4

Characterization of Distal Suppressors

Figure 8:
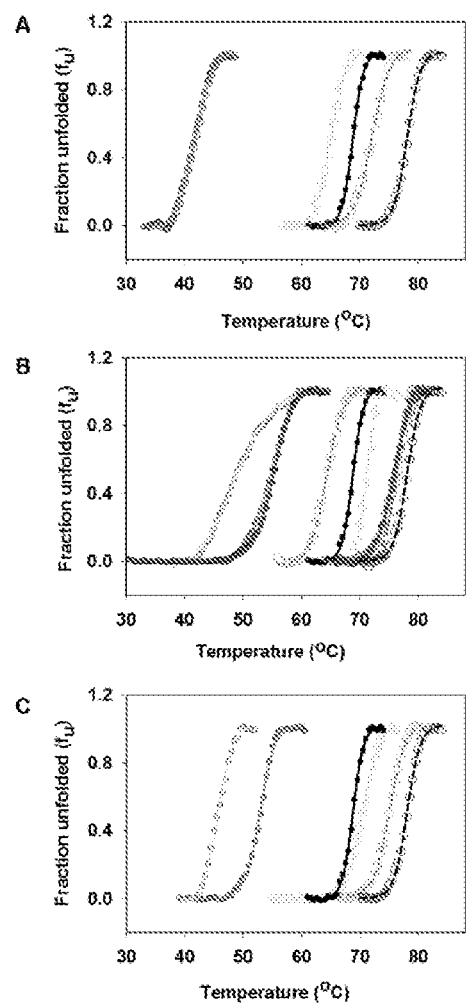
FIG. 8 depicts the thermal stabilities of purified CcdB variants, in accordance with an embodiment of the present disclosure.

The presence of the ligand, CcdA during thermal denaturation of CcdB, shifts the unfolding equilibrium towards the folded fraction of CcdB, resulting in an increased $T_m$ than when monitored in its absence (Table 3, FIG. 8). This increase in $T_m$ was observed for all mutants except R10G. L36A/R10G showed an increase of only 9° C. in the presence of CcdA while other mutants showed an increase of >20° C. These observations indicated a decrease in affinity of R10G CcdB for CcdA. The distal suppressors R10G and E11R are present on an exposed loop of CcdB and contact CcdA in the crystal structure of the CcdB-CcdA complex, PDB id 3G7Z (De Jonge, Garcia-Pino et al. 2009). R10 forms a hydrogen bond (2.9 Å) with N69 of CcdA. Hence, mutations at R10 and E11 are likely to destabilize binding of CcdB to CcdA, consistent with our results. The suppressor mutant, R10G has an increased stability relative to WT (R10G ($T_m$(R10G)=74.8±0.2° C., $T_m$(WT)=66.8±1.0° C., Table 3, FIG. 6D). However, the compromised ability to bind to its antitoxin CcdA results in increased toxicity in native contexts where CcdB and CcdA are both present. Thus, to maintain homeostasis in the system, evolutionary pressure defines a trade-off between function and stability of the protein (Schreiber, Buckle et al. 1994), settling on an optimally stable wild type protein rather than a maximally stable one. This explains why the R to G mutation is not found in naturally occurring CcdB homologs. The screen employed in this work identifies stabilizing variants which are functionally competent to bind to only one of the binding partners, DNA Gyrase, explaining the identification of the R10G like mutation. To understand the molecular mechanism(s) by which R10G rescues L36A present at the core, we examined if any long range functional interaction was predicted between the sites by the program SCA (Halabi, Rivoire et al. 2009). No interaction was seen although this analysis was limited by low sequence diversity of CcdB. Experimentally, we observed that R10G stabilized the WT protein and other PIMs while the E11R substitution stabilized the PIM V20F. The large conformational flexibility of glycine (in case of R10G) might stabilize the loop harboring residue 10 by accessing conformations not accessible to other residues. Further experiments need to be done to understand the mechanism of stabilization of the PIM V20F by E11R and to determine if E11R, like R10G also functions as a global suppressor.

Example 5

ContactScore as a Model Discriminator

Figure 9:
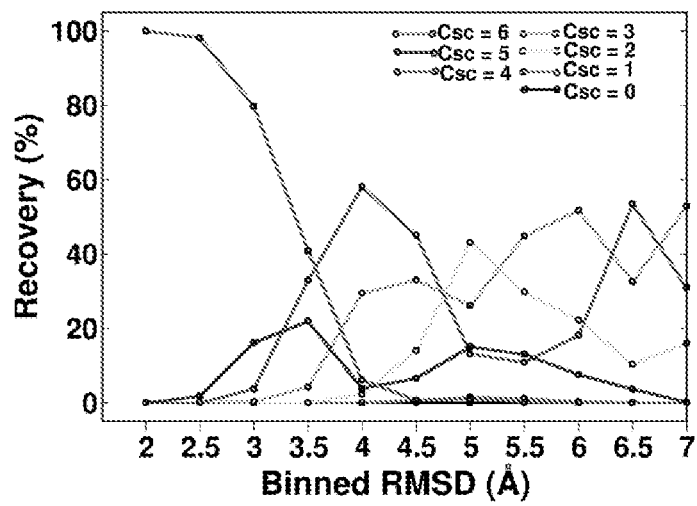
FIG. 9 depicts the recovery of CcdB models as a function of different ContactScore values, in accordance with an embodiment of the present disclosure.
Figure 10:
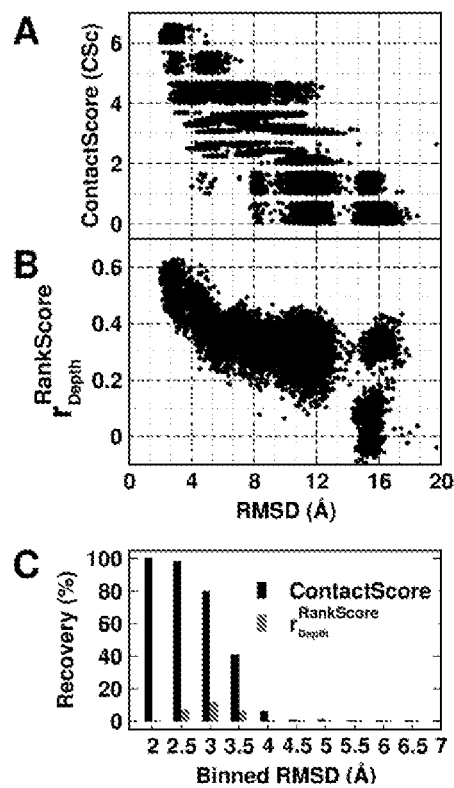
FIG. 10 depicts the experimentally determined "ContactScore" as model discriminators, in accordance with an embodiment of the present disclosure.

A decoy set of 10,659 models (Adkar, Tripathi et al. 2012) of CcdB was used to probe the utility of the experimentally obtained contact information in model discrimination. The decoy set contained models ranging from 1.9-20.4 Å (backbone RMSD relative to the crystal structure, PDB id 3VUB (Loris, Dao-Thi et al. 1999)). The models were scored based on ContactScore (Csc), which was defined as the number of times the experimentally identified residue contact pairs (6 pairs) are within a cutoff distance of 7 Å of each other in a given model. CSc is an integral value ranging from 0 to 6 since there are six (PIM, proximal suppressor) pairs. Proximal suppressor mutants are likely to have their side chains facing towards the corresponding PIM (FIG. 5B-F), and hence the side chain centroids of the pair are likely to be closer than their corresponding Cα atoms. The distribution of recovery of models (defined as percentage of models selected by the metric within a specified RMSD range, in a pool of models) with respect to their backbone RMSD relative to the crystal structure (FIG. 9) shows the sensitivity of CSc and its relevance as a metric for model discrimination. Models satisfying all the experimental constraints i.e. CSc=6 are distributed in the RMSD bin <4A. The distribution progressively shifts towards a higher RMSD range with decrease in the number of constraints being satisfied (CSc<6). This emphasizes the sensitivity and selectivity of the metric. The correlation coefficient of a plot of RankScore as a function of residue depth in a model, $r_{depth}^{Rankscore}$ (or $r_{depth}^{score}$) has been previously used as a model discriminator (Adkar, Tripathi et al. 2012). $r_{depth}^{score}=0.6$ for the native structure of CcdB. Thus, models with $r_{depth}^{score} \geq 0.6$ were selected as "correctly folded models" when $r_{depth}^{score}$ was used as the metric. A comparison of the two metrics shows that CSc performs significantly better than $r_{depth}^{score}$, recovering 100%, 98% and 80% structures in backbone RMSD ranges 1.5-2 Å, 2-2.5 Å and 2.5-3 Å respectively, while the latter recovered 0%, 7% and 12% in the above ranges (FIG. 10). CSc and $r_{depth}^{score}$ identified 585 and 67 models respectively with RMSD range <4 Å from the decoy set (FIG. 10A, B). Thus, CSc is able to recover 66% of native-like models (RMSD <4A) from the dataset as compared to only 8% by $r_{depth}^{score}$.

The decoy discrimination efficiency of $r_{depth}^{score}$ and CSc was compared with another method which uses a simple scoring function based on residue accessibility in globular proteins (Bahadur and Chakrabarti 2009). The function (Rs) evaluates the deviation from the average packing properties of all residues in a polypeptide chain corresponding to a model of its three-dimensional structure (Bahadur and Chakrabarti 2009). The parameter Rs was calculated for the CcdB decoy set. Since Rs estimates deviation from the average Accessible Surface Area (ASA), the native structure should ideally possess the lowest value of Rs. However, when the CcdB decoy set was sorted according to the Rs values, the native structure was ranked 934$^{th}$ and the correlation between RMSD and Rs was seen to be only 0.3. These data demonstrate that both $r_{depth}^{score}$ and Contact score (CSc) parameters derived from mutational data perform better depth than simple solvent accessibility based correlations such as the one observed above.

Example 6

Application of Suppressor Methodology to Identify the Functional Confirmation of Membrane Protein DgkA In Vivo The structures of the integral membrane protein, DgkA solved by X-Ray crystallography (Li, Lyons et al. 2013) and NMR (Van Horn, Kim et al. 2009) are different from each other in important respects. The NMR structure appears to be in a domain swapped conformation relative to the crystal structure. Several pairs of differential contacts serve to discriminate the two structures, including contacts made by residues V62, M66, I67, V68 and W112 (Table 4, FIG. 11, 12). Consequently residues in proximity to each of these residues in the X-Ray structure (PDB id 3ZE5 (Li, Lyons et al. 2013)) are distant in the NMR structure (PDB id 2KDC (Van Horn, Kim et al. 2009)). Thus by constructing PIM's at the above positions and isolating corresponding suppressors, it should be possible to determine which of the two structures represents the functional conformation in-vivo. It has previously been shown (Raetz and Newman 1978; Raetz and Newman 1979) that cells deleted for dgkA do not grow under conditions of low osmolarity, providing a facile screen for both PIM's and their corresponding suppressors.

Figure 11:
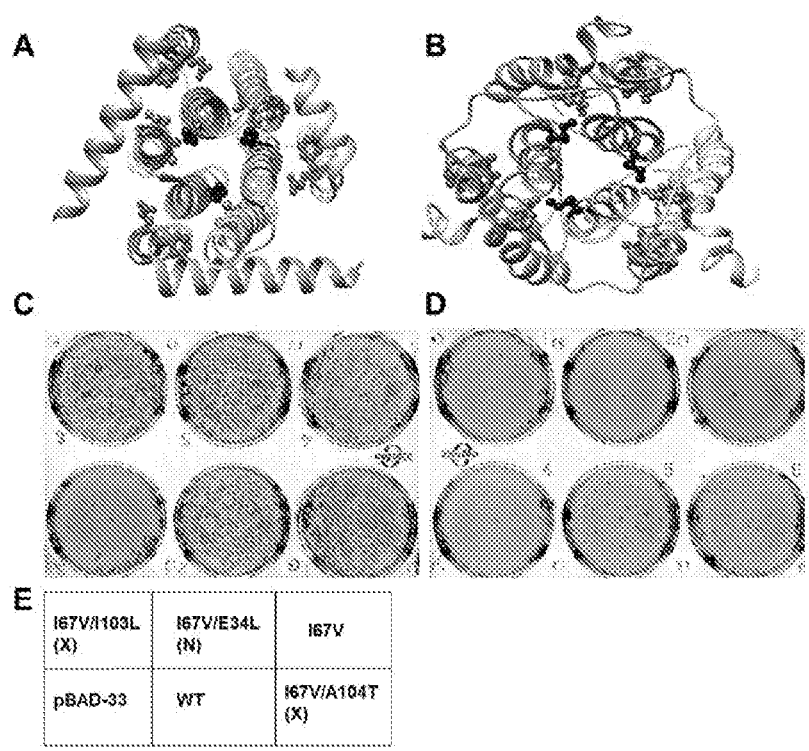
FIG. 11 depicts the screening of suppressors for the PIM I67V DgkA, in accordance with an embodiment of the present disclosure.
Figure 12:
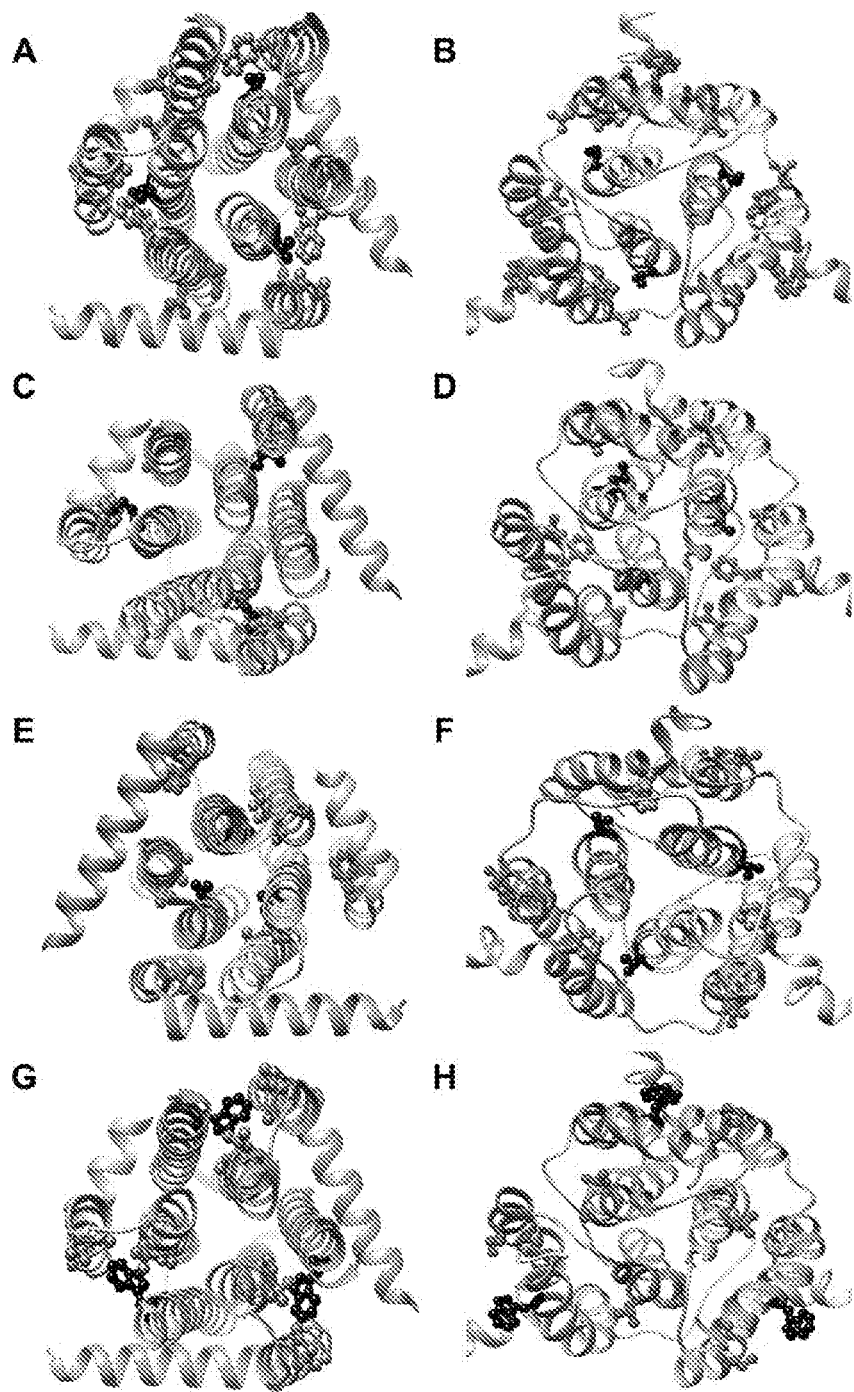
FIG. 12 depicts the differential contact residue pairs mapped onto structures of DgkA, in accordance with an embodiment of the present disclosure.
Figure 13:
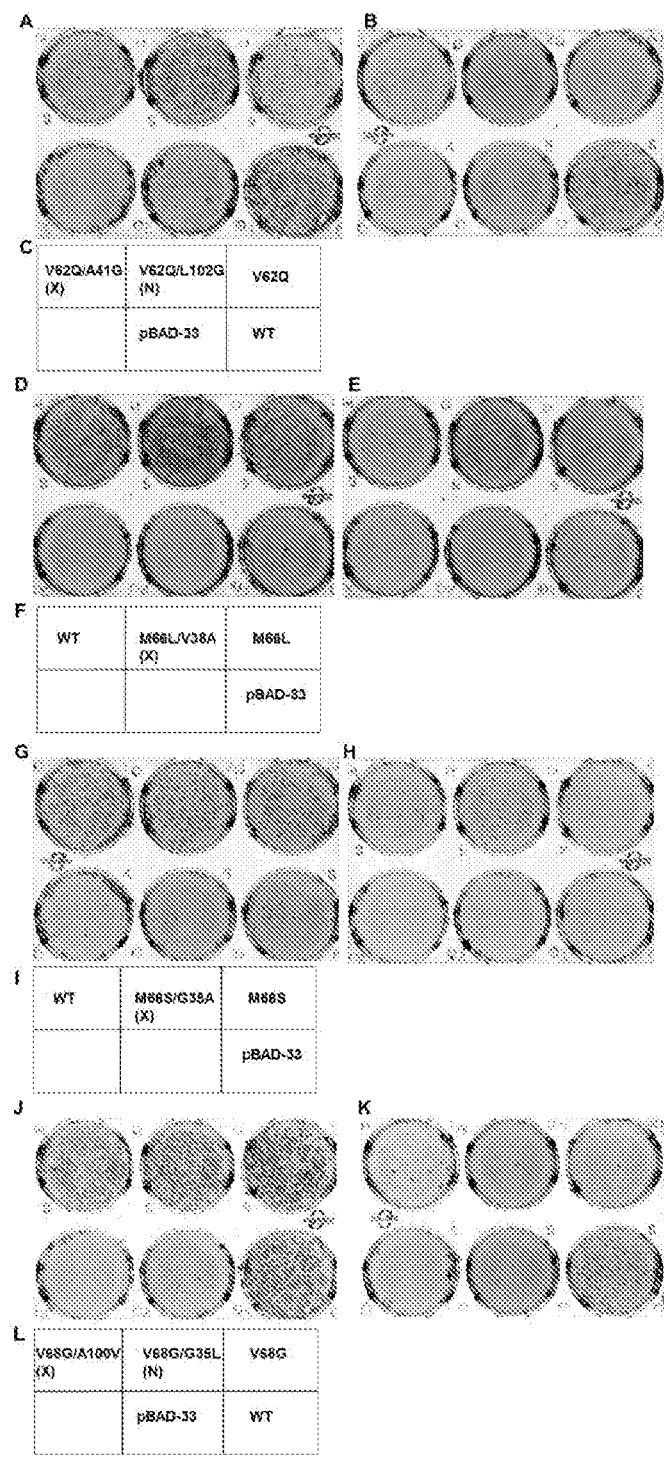
FIG. 13 depicts the screening for suppressors of PIMs of DgkA, in accordance with an embodiment of the present disclosure.

V62Q, M66S, M66L, I67V, V68G and W112V were identified as PIMs from screening of SSM libraries constructed at these positions. For these mutants, colonies appeared on plates only at high osmolarity (NaCl concentrations of 0.15%, 0.15%, 0.15%, 0.03%, 0.15% and 0.15% respectively) after 12 hrs of incubation at 37° C., as opposed to cells expressing WT DgKA which grew even at 0% NaCl. Second-site suppressor mutagenesis libraries in which each residue in contact with the PIMs in both NMR and crystal structures was individually randomized, (Table 4) were screened for growth under low salt conditions. At all selected PIMs, suppressors were found only at those positions in contact with the PIM in the X-Ray structure (i.e. V62Q/A41G, M66L/V38A, M66S/G35A, I67V/I103L, I67V/A104T and V68G/A100V), with none coming up from the NMR set (FIG. 11, 13, Table 4). The only exception was for the PIM W112V, where no suppressors were experimentally identified, possibly due to the large change in volume for the PIM relative to the WT residue. The data reported here are consistent results obtained from more than five independent experiments for each mutant. The results strongly suggest that the crystallized conformation is the native, functional conformation in-vivo.

Example 7

Computational Approaches to Predict Spatially Proximal Residues

Figure 14:
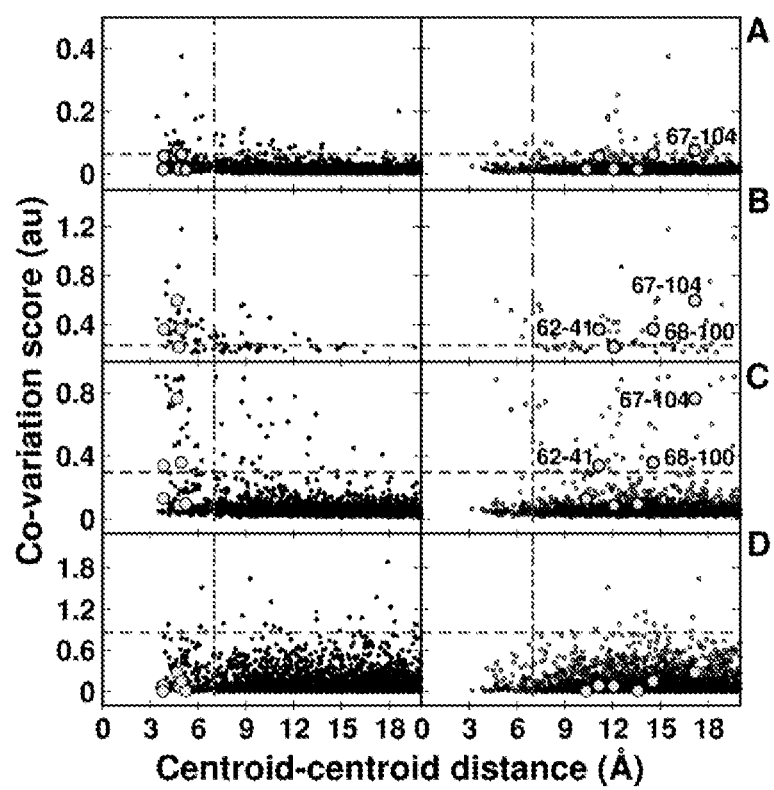
FIG. 14 depicts the computational analyses of co-varying residues for DgkA and comparison with experimentally determined contact residue pairs, in accordance with an embodiment of the present disclosure.

In the recent past there have been several computational efforts to identify residues in contact, involving analysis of correlated substitution patterns in an MSA of a protein. DCA (Morcos, Pagnani et al. 2011), PSICOV (Jones, Buchan et al. 2012; Nugent and Jones 2012), GREMLIN (Kamisetty, Ovchinnikov et al. 2013) and SCA (Halabi, Rivoire et al. 2009) analyze co-variation matrix data from an MSA to deduce residues in contact. The methods rank residue pairs based on a co-variation or correlation score specific to each method. The top ranked pairs are predicted to be in contact. The methods perform well when the size of the MSA is large i.e. >5L (L is the length of the protein) (Kamisetty, Ovchinnikov et al. 2013). DgkA (121 residues per protomer) exhibits large sequence diversity (4175 sequences in MSA). Some high scoring co-varying pairs predicted by DCA, GREMLIN and PSICOV were found to be true contacts (centroid-centroid distance <7 Å, FIG. 14) when mapped onto the crystal structure. However, there were other high scoring pairs which were either far apart in the X-Ray structure (predictions by PSICOV) or were in proximity when analyzed with the NMR structure (predictions by GREMLIN and PSICOV). These might either be false positives or might suggest that both the conformations (present in X-Ray and NMR structures respectively) are populated in-vivo. Of the six contacts identified from our suppressor analyses (Table 4), three (62-41, 67-104, 68-100) were predicted in the top L/2 co-varying pairs by GREMLIN and PSICOV (FIG. 14), only 67-104 was predicted by DCA and none by SCA.

Figure 15:
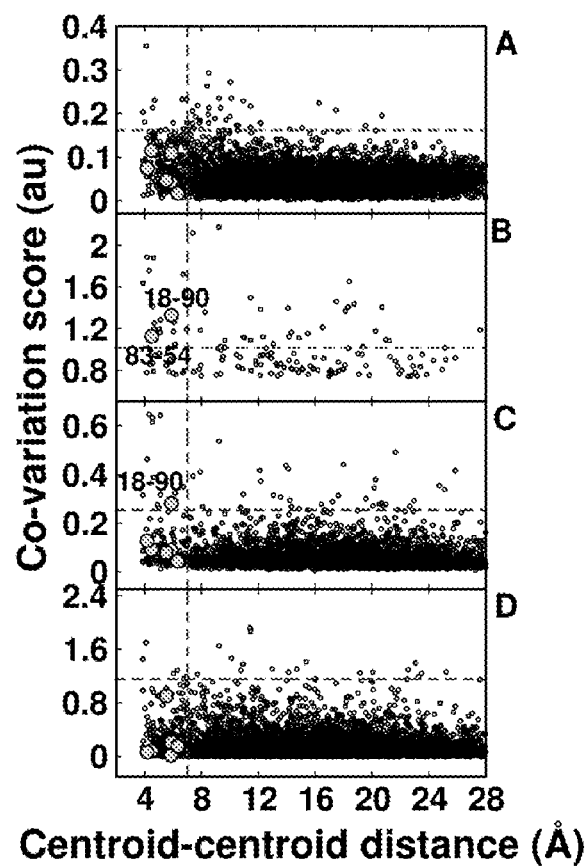
FIG. 15 depicts the computational analyses of co-varying residues for CcdB and comparison with experimentally determined contact residue pairs, in accordance with an embodiment of the present disclosure.

The computational predictions become less reliable for proteins with few homologs. CcdB (101 residues per protomer) has 350 sequences (<5L) in the MSA when searched against the nr database. Residue pair 18-90 is predicted in the top L/2 covarying mutations by PSICOV and GREMLIN, while 83-54 is predicted only by GREMLIN (FIG. 15). Computational approaches fail to capture most contact pairs which are experimentally identified by us. Many predicted contact pairs in the top L/2 predictions observed from analysis of the MSA have high centroid-centroid distances. In contrast, all contact pairs identified experimentally by us (both in case of CcdB and DgkA) have centroid-centroid distances <7 Å. Many of these contact pairs could not have been deduced from existing sequence co-variation data.

Example 8

ΔΔG Calculations for Local Suppressors of CcdB

Figure 16:
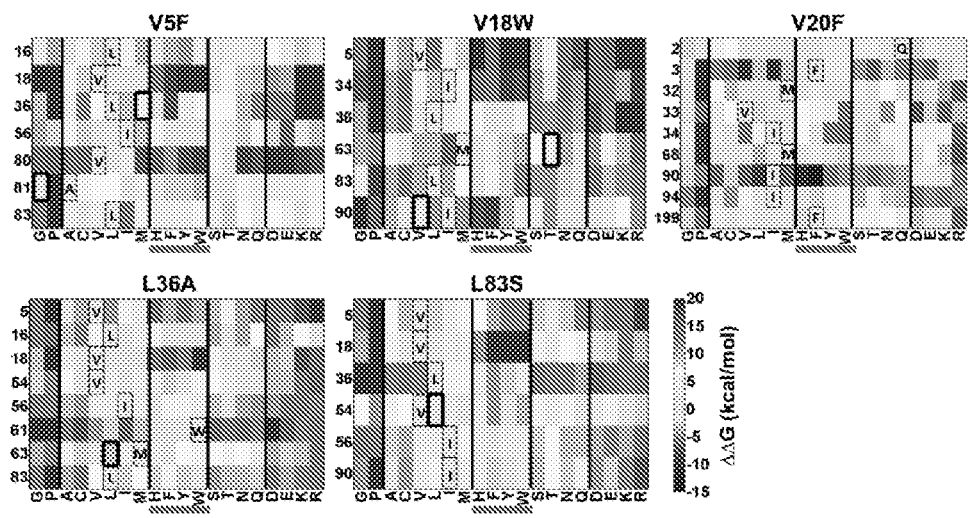
FIG. 16 depicts the heatmaps showing calculated values of $\Delta\Delta G$ using Rosetta for double mutants of CcdB, in accordance with an embodiment of the present disclosure.

There is considerable interest in accurate prediction of mutational effects on the free energy of folding (Guerois, Nielsen et al. 2002; Shen and Sali 2006; Kellogg, Leaver-Fay et al. 2011). We therefore explored if ΔΔG calculations could be used to rationalize the identity of the experimentally observed local suppressors. To this end the difference in stability between the (PIM, suppressor) pair and the PIM for CcdB mutants was calculated. $\Delta\Delta G_{folding}$ ($\Delta G_{folding}$Double mutant $-\Delta G_{folding}$PIM) was calculated using Rosetta v3.3 (Kellogg, Leaver-Fay et al. 2011). Putative suppressors were considered to be all residues within 7 Å (side chain-side chain centroid distance) of the PIM. Many stable substituents were predicted ($\Delta\Delta G_{folding}$<0, FIG. 16). However, amongst the six experimentally identified stable compensatory pairs, only L36A/M63L (−3.7 kcal/mol) was predicted to be stable. The remaining five contact pairs were predicted to be either marginally stable or unstable. Several other mutations besides the experimentally determined ones were predicted to be stabilizing e.g. V5F/L16G, V18W/I90A, V20F/I90A, L36A/V54I and L83S/V18I. These might be present in the earlier rounds of sorting but are lost in later rounds due to stringent sort conditions. A marked bias for aromatic substitutions was observed in the predictions (FIG. 16, substitutions underlined in magenta) though such aromatic substitutions were not observed experimentally. Aromatic substitutions are rigid and were found to over pack the cavity created by the PIMs in the models generated using Rosetta. Further, several of the mutations that were computationally predicted to be highly stabilizing are unlikely to be so as they are not complementary to the original PIM, e.g. L36A/W61F, V5F/L16Y, V18W/I90F and V20F/I90F. If aromatic substitutions are excluded, Rosetta predictions using ΔΔG values are in reasonable qualitative agreement with experiment.

Figure 17:
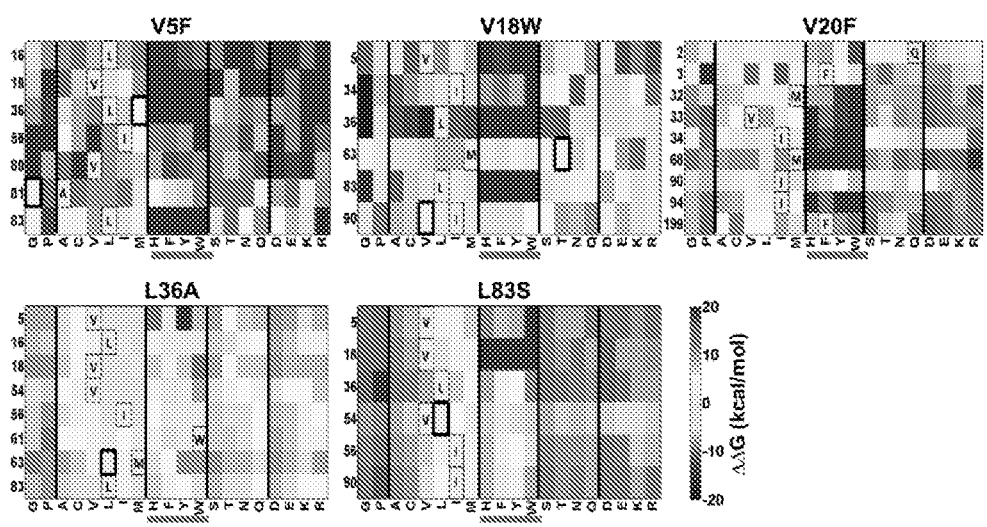
FIG. 17 depicts the heatmaps showing calculated values of $\Delta\Delta G$ using FoldX for double mutants of CcdB, in accordance with an embodiment of the present disclosure.

A similar analysis was done using FoldX (Guerois, Nielsen et al. 2002) (FIG. 17). However, these predictions were in poorer agreement with the experimental results, compared to those of Rosetta. Thus, in addition to their use in protein structure prediction, results from such suppressor analyses can also be used to benchmark and improve computational approaches to predict mutational effects on protein stability.

Discussion of Results from Examples 1-8

Interactions at the protein core are important in determining its structure and stability. The saturation-suppressor mutagenesis methodology described here (FIG. 1, 3) enabled identification of 12 residues at the hydrophobic core and their pairwise interactions (FIG. 5A, F) placing important constraints on packing of the model protein CcdB. There may be mutations in the core which allow the protein to fold but are functionally defective (Roscoe, Thayer et al. 2013). We eliminated such mutations as the screen required variants to both fold into a stable conformation and be functionally active to bind to Gyrase. The experimentally identified residue pairs for CcdB are in physical contact and have suppressor positions common to each other (Table 2, FIG. 5B-F). This interlinked network of residues restricts the conformational space during folding. The ContactScore metric defined above selects models satisfying the identified spatial constraints. A histogram of recovery of models with respect to backbone RMSD of the models selected by this metric shows a maximum of 100% for models with backbone RMSD <2 Å, gradually decreasing to 66% for models <4 Å and subsequently plateauing to 0% for models >5 Å, reflecting the sensitivity and accuracy of the parameter. A high recovery is important for protein model discrimination, as typically there will be very few low RMSD models in the candidate set of predictions. The ContactScore metric also performs better than a simpler approach based on deviation of residue accessibilities in a model from their average values in a large dataset of proteins (Bahadur and Chakrabarti 2009).

The approach was extended to the important case of membrane proteins. Many membrane proteins adopt multiple conformations (Tokuriki and Tawfik 2009) and membrane mimetics used to solubilize and stabilize membrane proteins can affect their conformations (Cross, Murray et al. 2013). There are two reported structures of the integral membrane protein DgkA solved by X-Ray crystallography (Li, Lyons et al. 2013) and solution NMR (Van Horn, Kim et al. 2009) which differ significantly from each other. Using our suppressor methodology, we unambiguously identified six residue-residue contacts which were all present in the crystal structure but were spatially distant in the NMR structure. This suggests that the conformation of the protein in the lipidic (monoacylglycerol) cubic phase conditions (used in X-Ray crystallography (Li, Lyons et al. 2013)) is the functional conformer in-vivo and is not an artifact resulting from the presence of thermostabilizing mutations and minor distortions that might result from crystal contacts. Our results are also consistent with a recent reanalysis of oriented sample solid state NMR data for the protein in liquid crystalline bilayers (Murray, Li et al. 2014) which showed better overall agreement with the crystal than with the solution NMR structure.

Broad application of suppressor methodology to systems where no structural information is available requires accurate discrimination of buried from exposed active-site residues and of distal from proximal suppressors. As discussed above, buried and active-site residues can be distinguished based on their mutational sensitivity patterns as well as from data on mutant protein levels, sensitivity to chaperone overexpression patterns (Tokuriki and Tawfik 2009) and residue conservation patterns (Melamed, Young et al. 2015). Distal suppressors are likely to be on the surface (Bank, Hietpas et al. 2015). The correlation of mutational sensitivity with depth seen for CcdB should allow distinction of local and global suppressors for other globular proteins as well, as long as the majority of global suppressors lie on the surface. Unlike globular proteins, little is known about sensitivity to mutation in membrane proteins or natively unfolded proteins. Until such data becomes available it will be challenging to apply this methodology to these systems. In the case of DgkA, we had the much simpler objective of distinguishing between two possible structures. While distinguishing between global and local suppressors maybe more challenging in membrane proteins, given sufficient double mutant data, it should be straightforward because each global suppressor should suppress a much larger number of PIMs than all local suppressors. The average relative frequency of obtaining proximal versus distal suppressors is currently unknown. If a single-site saturation mutagenesis library is enriched for inactive mutants (PIMs), subjected to random mutagenesis and screened for suppressors, the resulting population will be enriched for global suppressors (Bershtein, Segal et al. 2006; Bershtein, Goldin et al. 2008). This is because a global suppressor will suppress multiple PIMs. However, for a specific PIM, it is not obvious that global suppressors will dominate. A recent study examined a library of the 75 amino acid RRM domain of the yeast poly-A binding protein (Melamed, Young et al. 2013). Functional scores for 1246 single and 39,912 double mutants were obtained. Epistatic interactions were enriched for residue pairs with short sequence spacing (<5) and short distance (10-15 Å). Another recent study reported exhaustive screening of single and double mutants of GB1 (Olson, Wu et al. 2014). The majority of pairs displaying positive epistasis had $C\beta$-$C\beta$ distances <8 Å. Both of the above studies indicate that local suppressors may occur at higher frequency than global ones with respect to individual PIMs but more data is required to confirm this.

Experimental approaches discussed previously to identify second-site suppressors used random mutagenesis and/or directed evolution to generate suppressor libraries. Although these libraries have high diversity and mutations at multiple residue positions, they typically do not have more than a single base substitution at any codon. It should be noted that single base changes can sample only 39% of all possible amino acid substitutions. Hence, they do not exhaustively sample all possible second-site suppressors for a given inactivating mutation. This is important, since for a given PIM there appear to be only a few local suppressors, and these could well be absent in a library generated by conventional random mutagenesis. Computational approaches to identify spatially proximate residues require a large number of homologous sequences to be present (greater than five times the length of the protein) (Kamisetty, Ovchinnikov et al. 2013). These approaches do not work well for proteins like CcdB due to limited evolutionary diversity in the MSA. Even for the protein DgkA, for which there are several sequences, the four computational methods gave differing predictions, several likely false-positive contacts and did not identify several of the contacts identified by our suppressor approach. Our approach, thus provides complementary information to these existing methods, and can be usefully combined with them to guide protein structure prediction. The approach described here uses saturation-suppressor mutagenesis to identify spatially proximate residues. The library generation design adopted here for CcdB constructs the second-site saturation library in the background of individual inactive mutants chosen from a single-site saturation mutagenesis library comprising of ~1430 mutants of CcdB (Adkar, Tripathi et al. 2012).

Second-site suppressors can be either proximal or distal to the mutation site. Virtually all suppressors identified in the study (for CcdB) increased the thermal stability relative to the original PIM. Proximal suppressors are likely to ameliorate packing defects and hence restore stability. These have previously been reported to restore activity (Machingo, Mazourek et al. 2001), increase thermal stability and restore packing (Pakula and Sauer 1989). Residues distant from the site have previously been found to function by either increasing global thermodynamic stability (Pakula and Sauer 1989; Bershtein, Goldin et al. 2008; Araya, Fowler et al. 2012), increasing activity of the wild type protein without any substantial increase in stability (Hecht and Sauer 1985) or improving foldability without much effect on the thermodynamic stability (Sideraki, Huang et al. 2001). In the present study, suppressors could be obtained for each of the five PIMs in CcdB and five of six PIMs in DgkA, regardless of the location and nature of the PIM. The distal suppressor R10G in CcdB increased the $T_m$ by 8° C., relative to WT CcdB (Table 3) which rescues the destabilized mutant L36A.

Global suppressors have been shown to often comprise consensus/ancestral mutations (Bershtein, Goldin et al. 2008). We analyzed the consensus/ancestral mutations for CcdB. The consensus sequence was obtained from an MSA of 350 homologs using MATLAB and the ancestral sequence was obtained using the FastML server (Ashkenazy, Penn et al. 2012). The likely global suppressors we obtained in the present study are R10G, E11R and E11K. At R10 the ancestral and consensus amino acids are P and R respectively and at E11 they are A and N respectively. Hence, at least for these two positions, the ancestral/consensus amino acids were different from the experimentally obtained suppressors. Further experiments are required to ascertain whether the ancestral/consensus amino acids will also act as global suppressors.

Advances in the field of protein structure prediction integrate various computational approaches with distance restraints derived from cross-linking experiments and mass spectrometry (Young, Tang et al. 2000), sparse NOE data (Bowers, Strauss et al. 2000; Li, Zhang et al. 2003; Thompson, Sgourakis et al. 2012), residual dipolar coupling data (Haliloglu, Kolinski et al. 2003; Qu, Guo et al. 2004), chemical shift data (Shen, Lange et al. 2008) from NMR experiments, co-varying residues identified from statistical analysis of genomic data (Hopf, Colwell et al. 2012; Nugent and Jones 2012; Sulkowska, Morcos et al. 2012; Ovchinnikov, Kamisetty et al. 2014) to determine structure. The combination of site-directed mutagenesis or doped oligonucleotide based synthetic library generation strategies with deep sequencing has expanded the contours of understanding sequence, structure, function relationships (Tripathi and Varadarajan 2014). High resolution mutational analyses using single-site saturation mutagenesis have facilitated understanding the influence of each residue on a protein's structure, stability, activity, specificity and fitness (Fowler, Araya et al. 2010; Adkar, Tripathi et al. 2012; Roscoe, Thayer et al. 2013; Tripathi and Varadarajan 2014). Expanding this landscape by integrating spatial constraints isolated from paired mutational phenotypes can greatly advance our efforts to construct highly accurate structural models without the need for any evolutionary information. However, unbiased examination f all pairwise mutant combinations is currently not feasible because the large library size cannot be sequenced at sufficient depth using deep sequencing ($^{100}C_2 \times 400$ or $2 \times 10^6$ for a 100 residue protein (Tripathi and Varadarajan 2014)). The methodology outlined here can be similarly applied to any protein or protein complex where mutation can be coupled to a phenotypic readout. In these proof of principle studies, mutant identities were determined after single (DgkA) or multiple (CcdB) rounds of screening, using Sanger sequencing. However, as with earlier studies using single mutant libraries (Fowler, Araya et al. 2010; Tripathi and Varadarajan 2014), enrichment of mutant pairs at each stage can be monitored using deep sequencing, which in turn may provide additional constraints to guide macromolecular structure prediction and determination. These efforts may prove beneficial in resolving the gap between protein sequence and structure and also in the isolation of mutants with improved stability and foldability, relative to WT.

Example 9

Materials and Methods

CcdB Double Mutant Library Construction:

An SSM library of CcdB (Jain and Varadarajan 2014) was cloned in a Yeast Surface Display (YSD) vector pPNLS (Bowley, Labrijn et al. 2007) between SfiI sites. In this background, various single-site mutants were made by three fragment recombination of gapped ve$^{cto}$r $_a$nd two overlapp$^{in}$g CcdB fragments. PCR to amplify the overlapping fragments of CcdB was carried out with Phusion DNA polymerase (Finnzymes) for 15 cycles with 1-5 pg template DNA. pPNLS vector containing a ~1 kb stuffer sequence was digested with SfiI (New England Biolabs, NEB) to remove the stuffer insert, and gel purified. The digested vector and the two CcdB fragments were transformed by three fragment homologous recombination in *Saccharomyces cerevisiae* EBY100 (Gietz and Schiestl 2007). Yeast cells were incubated for 3 hrs at 30° C. in 30 ml YPD broth after transformation. The cells were washed twice with 30 ml sterile water and grown in 500 ml SDCAA for 32 hrs at 30° C., 250 rpm. The total number of transformants was estimated by plating a small amount of the transformed cell suspension (30 μl of 30 ml) on an SDCAA agar plate and multiplying the number by the dilution factor. Cells representing 100 times the total transformants obtained were re-grown in 300 ml SDCAA for 16-20 hrs at 30° C., 250 rpm and stored in aliquots of $10^9$ cells in YPD (HiMedia) containing 25% glycerol at −70° C.

Yeast Surface Display and Selection of Second Site Suppressor Mutants:

Inactive mutants and corresponding double mutant libraries cloned in pPNLS were displayed on the surface of yeast (Chao, Lau et al. 2006) at either 30° C. (L36A, L83S parent and mutant libraries) or 20° C. (VSF, V18W, V20F parent and mutant libraries) for 16 hrs for all experiments related to yeast surface display described here. Binding of chicken anti-HA antibody (SIGMA, 1:300) to the HA tag at the N terminus of CcdB was used to monitor surface expression of the displayed protein. Goat anti-chicken IgG conjugated AlexaFluor-488 (Invitrogen, 1:300) was used as the secondary antibody. The cmyc tag fused to the C terminus of CcdB in the pPNLS vector was removed to enable binding of the ligand Gyrase, which has a 3×FLAG tag at its C terminus. Gyrase binding was assessed by binding of mouse anti-FLAG antibody (SIGMA, 1:300) and rabbit anti-mouse IgG conjugated AlexaFluor-633 (Invitrogen, 1:1,800) secondary antibody. ~$10^7$ double labeled cells from each library were sorted on a BD FACS Aria-III flow cytometer (488 nm, 633 nm lasers for excitation and 530/30 nm, 660/20 nm bandpass filters respectively for emission) to enrich mutants which show better surface expression and binding than the reference parent inactive mutant. The concentration of Gyrase-3×FLAG used depended on the corresponding affinity of the reference inactive mutant. Equilibrium dissociation constant values ($K_d$) for the reference mutants were measured using a YSD titration as described (Chao, Lau et al. 2006). Sorting of the libraries was carried out for multiple rounds till (i) analysis of the population grown after the final sort showed at least 10% of the population in a gate which contained 0% of the corresponding PIM (FIG. 4, panel showing L83S-lib after sort3), and (ii) there was no further improvement in signals from the enriched library with subsequent rounds of sort. The stringency of the sort was progressively increased by decreasing the concentration of Gyrase and gating the top ~1% of the population, which largely excluded the reference mutant (see Table 1).

Identification of Suppressor Mutants:

Yeast cells harvested from 25 ml saturated culture of sorted libraries were resuspended in buffer P1 (supplied with Qiagen plasmid miniprep kit) and vortexed in the presence of acid-washed glass beads (SIGMA) for 10 minutes. The suspension was incubated with Zymolyase (30 U, G-Biosciences) at 37° C. for 4 hrs to break the cell wall. Qiagen plasmid miniprep kit was used for further downstream processing of the cells to purify the plasmid. CcdB gene inserts amplified from the libraries were cloned into pTZ57R/T TA vector using InsTAclone PCR cloning kit (Thermo Scientific) and transformed into *E. coli* XL1-Blue cells for blue-white screening (Langley, Villarejo et al. 1975). The CcdB inserts from 96 randomly picked white colonies derived from each library after the final round of sorting, were sequenced by Sanger sequencing at Macrogen, Korea to identify second-site suppressors.

Purification and Thermal Denaturation of CcdB Mutants:

The ccdb gene initially cloned in pPNLS vector was cloned into pBAD-24 bacterial expression vector by Gibson assembly (Gibson, Young et al. 2009). *E. coli* CSH501 cells are resistant to the toxin CcdB due to mutation in the chromosomal copy of gyrA which eliminates binding between CcdB and DNA Gyrase; the strain was kindly provided by Dr. M Couturier (UniversiteLibre de Bruxelles, Belgium). These cells, transformed with pBAD-24-CcdB plasmid were inoculated in 200 ml LB medium, grown till $OD_{600}$ 0.7 at 37° C., induced with 0.2% arabinose and grown for an additional 12 hrs at 18° C. The cells were harvested at 4,000 rpm for 10 min at 4° C., resuspended in 25 ml resuspension buffer (0.05M HEPES, pH 8.0, 1 mM EDTA, 10% glycerol), containing 200 μM PMSF. The cells were lysed by sonication on ice. The solution was centrifuged at 14,000 rpm, for 30 min, at 4° C. The supernatant was loaded onto the pre-equilibrated CcdA (residues 46-72) affinity column (prepared using Affigel-15, Biorad, as per instructions in the manual), and incubated for 4 hrs at 4° C. The column was washed thrice with 20 ml coupling buffer to remove the unbound protein and eluted with 0.2M Glycine, pH 2.5 in equal volume of 400 mM HEPES, pH 8.5 and concentrated using Centricon centrifugal filter unit (Millipore, MW cut-off 3 kDa). Fluorescence based thermal shift assay (TSA) was carried out on an iCycle iQ5 Real Time Detection System (Bio-Rad, Hercules, Calif.). 25 μl of the reaction mixture containing 404 CcdB purified protein, 25× Sypro orange dye and buffer (200 mM HEPES and 100 mM glycine, pH 7.5) was subjected to thermal denaturation on a 96-well iCycleriQ PCR plate, from 20° C. to 90° C. with an increment of 0.5° C./min. Denaturation of the protein was also carried out in the presence of 20 μM CcdA peptide (residues 46-72). Sypro orange binds to the exposed hydrophobic patches of a protein, leading to an increase in observable fluorescence of the dye as the protein unfolds (Niesen, Berglund et al. 2007). The data was fitted to a standard four parameter sigmoidal equation $y=LL+((UL-LL)/(1\pm e^{(Tm-T)/a}))$ using SigmaPlot™v11.0, where y is the observed fluorescence signal, LL and UL are the minimum and maximum intensities respectively during the transition, a is the slope of the transition, $T_m$ is the melting temperature (midpoint of the thermal unfolding curve or the temperature at which 50% of the protein is unfolded) and T is the experimental temperature.

Contact Score:

10,659 models for CcdB were generated as described (Adkar, Tripathi et al. 2012). Each model (m) was allotted a ContactScore (CSc) defined as, $$ContactScore_m = \sum_{i=1}^{n} S_i(x, y)$$

where, $S(x,y)=1$ if distance between the side chain centroids of residues x and y is <7 Å in the crystal structure of CcdB (PDB id 3VUB (Loris, Dao-Thi et al. 1999)) else S=0, n denotes the number of experimentally determined probable contact pairs, (x,y).

Calculation of the Rs parameter: The function (Rs) (Bahadur and Chakrabarti 2009) evaluates the deviation from the average packing properties of all residues in a given structural model. Rs is calculated using the following formula, where $ASA_{xi}$ and $\langle ASA_x \rangle$ are the accessible surface area values of residue X at position i and the average ASA of residue X in a large dataset, respectively (Bahadur and Chakrabarti 2009).

$$R_s = \sum_{i=1}^{wholechain} \frac{|ASA_{xi} - \langle ASA_x \rangle|}{\langle ASA_x \rangle}$$

The Rs parameter was calculated for all the 10,659 models in the CcdB decoy set. The ASA was calculated using NACCESS (v2.1.1) (Hubbard 1992).

Covariation Analysis:

Alignments of homologous sequences of CcdB were constructed by the jackhammer package of HMMER 3 (on the world wide web at hmmer.janelia.org/search/jackhmmer) (Finn, Clements et al. 2011) with the number of iterations set to 3, E-value cut-off 1e-6, with a search against the nr database on the world wide web at www.ncbi.nlm.nih.gov). Duplicate rows and gaps in the target sequence were removed from the multiple sequence alignment (MSA) to yield a final set of 350 alignments. This protocol has been adopted from (Nugent and Jones 2012). The processed MSA was entered as input to DCA (Morcos, Pagnani et al. 2011), PSICOV (Jones, Buchan et al. 2012) and SCA (Halabi, Rivoire et al. 2009) with default parameters as mentioned in the respective software packages. GREMLIN web-server on the world wide web at gremlin.bakerlab.org) (Kamisetty, Ovchinnikov et al. 2013) was also used for analysis. The co-variation scores estimated by the above programs were used for analysis. Similar analysis was done for DgkA, with 4175 non-redundant homologous sequences in the MSA.

In-Silico Identification of Suppressor Mutants Using ΔΔGCalculations:

All 19 possible mutations were computationally introduced at residue positions whose side chain centroids were within 7 Å of the side chain centroid of the chosen parent inactive mutant (PIM) residues i.e. VSF, V18W, V20F, L36A and L83S. The high resolution protocol for ΔΔG calculation in Rosetta version 3.3 (Kellogg, Leaver-Fay et al. 2011) was used to calculate $\Delta\Delta G_{folding}$, where $$\Delta\Delta G_{folding} = \Delta G_{folding} \text{ (Double mutant)} - \Delta G_{folding} \text{ (PIM)}$$

Double mutants showing negative values of $\Delta\Delta G_{folding}$ were predicted to stabilize the PIM. The following command was used: ~/rosetta_source/bin/ddg_monomer.linuxgccrelease -in: file: s ~/min_cst_0.5.dimer_0001.pdb -in::file:fullatom -ignore_unrecognized_res-constraints::cst_file~/input.cst -database ~/rosetta_database/ -ddg::mut_fileresfile-ddg::iterations 50 -ddg::weight_filesoft_rep_design -ddg::local_opt_only false -ddg::min_cst true -ddg::ramp_repulsive true -ddg::sc_min_only false -ddg::mean false -ddg::min true -ddg::dump_pdbs true.

BuildModel protocol of FoldX version 3.6 beta (Guerois, Nielsen et al. 2002) was also used to calculate $\Delta\Delta G_{folding}$ for mutants. The side chains of the neighboring residues were optimized in order to accommodate the mutant side chain, without allowing backbone flexibility.

Identification of differential contacts in DgkA: In the present study, true contacts were identified using a side-chain-sidechain centroid distance ≤7Å as the cutoff, for both X-ray and NMR structures of DgkA. The NMR structure (PDB id 2KDC) has co-ordinates for 16 poses. For the figures and distances listed we used only the first pose. However, we calculated the Root Mean Square Fluctuations (RMSF) for each residue (Ca atom) taking the average structure as the reference structure. Greater fluctuations are observed near the N-terminus of the protein (residues 1 to 33). Hence, we did not consider differential contacts within this region. Since, the region beyond the first 33 residues shows low RMS fluctuations, we report sidechain-sidechain centroid distances for residues showing differential contacts with the PIM in the X-ray and the NMR $1^{st}$ pose structure. In Table 5, we report the closest distance amongst all the 16 poses between each PIM and all residues shortlisted in Table 4.

Residue pairs in contact in X-Ray (PDB id 3ZE5 (Li, Lyons et al. 2013)) and NMR (PDB id 2KDC (Van Horn, Kim et al. 2009)) structures of DgkA were identified using the CMA server (Sobolev, Eyal et al. 2005) on the world wide web at ligin.weizmann.ac.il/cma) with the default parameters and threshold value of 10Å². Helix definitions mentioned in corresponding PDB header files were used to eliminate the contact pairs present in the same helix. PIM positions (say, "X") were defined as residues common to the identified contact residue pair subsets in both structures, but with different partners (say, "Y") in the two structures. The following criteria were additionally used to select X, i.e. (i) charged residues (X) were removed (ii) X and Y should not be involved in side-chain hydrogen bonding with each other (iii) X should have ≥2 contact partners in at-least one of the structures (iv) Sequence separation between X and Y, $|X-Y|>30$ (v) $|Y_{NMR}-Y_{X-Ray}|>6$.

Cloning, Mutagenesis, and Isolation of PIMs and their Suppressors:

Gene sequence corresponding to a cysteine-less (C46A/C113A) form of DgkA (referred as WT here) (Van Horn, Kim et al. 2009) along with an upstream 30 bp RBS sequence (CTCGAGCCCGGGGTCGACGGCTCTGCGGGC) was synthesized and cloned between KpnI and PstI sites in the pBAD-33 vector (Guzman, Belin et al. 1995), under the AraC promoter at GenScript. Selected PIM positions were randomized by single site saturation mutagenesis using NNN codons, by inverse PCR (Jain and Varadarajan 2014). The amplicon was purified, phosphorylated (T4 Polynucleotide Kinase, NEB), ligated (T4 DNA Ligase, NEB), transformed into E. coli TOP10 cells, plated on SB (HiMedia) containing 2% NaCl, 34 µg/ml chloramphenicol and 50 µg/ml kanamycin and incubated at 37° C. for 12 hrs. E. coli BW25113, knocked out for the chromosomal copy of dgkA gene (Keio collection (Baba, Ara et al. 2006), id JW4002-1; F-, Δ(araD-araB)567, ΔlacZ4787(::rrnB-3), λ-, rph-1, Δ(rhaD-rhaB) 568, ΔdgkA737::kan, hsdR514) referred to as ΔdgkA, was used for screening PIMs and suppressors. Growth defective PIMs (i.e. capable of growth only in media with high osmolarity) were screened by replica plating on selective media (Wen, Chen et al. 1996) (1% tryptone, 0.5% yeast extract, 0.01% arabinose, 1.6% agar, 34 µg/ml chloramphenicol and 50 µg/ml kanamycin) at decreasing concentrations of NaCl (0.15%, 0.03%, 0.01%, 0.007% and 0%), at 37° C. for 12-16 hrs. Identities of the PIMs were confirmed by Sanger sequencing. Each PIM was used as template to randomize corresponding potential contact partners using the inverse PCR method discussed above, to construct X-Ray and NMR structure specific second-site suppressor mutagenesis libraries. Screening of the libraries was carried out on selective media at varying concentrations of NaCl (mentioned above). Probable suppressors were identified as those which appear before the appearance of the corresponding PIM on a plate at low NaCl concentration (<0.15%), i.e. restore the growth defect of the PIM. WT DgkA and the empty vector pBAD-33 were used as positive and negative controls, respectively. Second-site putative suppressors were identified by Sanger sequencing at Macrogen, Korea. Fresh transformation of individual suppressors into E. coli ΔdgkA strain and comparison of the phenotype with the corresponding PIM confirmed the result from the initial screen.

TABLE 1

(Summary of sort details for different libraries of CcdB)

| S. no. | PIM | Sort Round # | Input | Output | Gyrase (nM) | Relative population of PIM in sorted gate (%) | Relative library population in sorted gate (%) | Growth temp. (° C.) |
|---|---|---|---|---|---|---|---|---|
| 1 | V5F | 1 | V5F_Lib | V5F_Lib1 | 16,000 | 0.3 | 0.2 | 20 |
| | | 2 | V5F_Lib1 | V5F_Lib2 | 4,000 | 0 | 0.3 | |
| | | 3 | V5F_Lib2 | V5F_Lib3 | 64 | 0 | 0.7 | |
| 2 | V18W | 1 | V18W_Lib | V18W_Lib1 | 16,000 | 0.7 | 0.6 | 20 |
| | | 2 | V18W_Lib1 | V18W_Lib2 | 8,000 | 0.9 | 0.8 | |
| | | 3 | V18W_Lib2 | V18W_Lib3 | 4,000 | 0.1 | 1.5 | |
| | | 4 | V18W_Lib3 | V18W_Lib4 | 1,000 | 0.6 | 0.5 | |
| | | 5 | V18W_Lib4 | V18W_Lib5 | 16 | 0.1 | 0.9 | |
| | | 6 | V18W_Lib5 | V18W_Lib6 | 4 | 0 | 0.8 | |
| 3 | V20F | 1 | V20F_Lib | V20F_Lib1 | 8,000 | 2.2 | 0.3 | 20 |
| | | 2 | V20F_Lib1 | V20F_Lib2 | 2,000 | 1.6 | 0.8 | |
| | | 3 | V20F_Lib2 | V20F_Lib3 | 256 | 0.7 | 0.4 | |
| | | 4 | V20F_Lib3 | V20F_Lib4 | 16 | 0 | 0.6 | |
| | | 5 | V20F_Lib4 | V20F_Lib5 | 4 | 0 | 0.5 | |
| 4 | L36A | 1 | L36A_Lib | L36A_Lib1 | 4 | 0 | 0.6 | 30 |
| | | 2 | L36A_Lib1 | L36A_Lib2 | 2 | 0.1 | 0.8 | |
| | | 3 | L36A_Lib2 | L36A_Lib3 | 1 | 0.3 | 0.8 | |
| | | 4 | L36A_Lib3 | L36A_Lib4 | 0.25 | 0 | 1.9 | |
| 5 | L83S | 1 | L83S_Lib | L83S_Lib1 | 4 | 6.8 | 0.4 | 30 |
| | | 2 | L83S_Lib1 | L83S_Lib2 | 1 | 0.1 | 0.3 | |
| | | 3 | L83S_Lib2 | L83S_Lib3 | 0.25 | 0 | 0.7 | |

TABLE 2

(Experimentally determined (PIM, suppressor) pairs for CcdB occur at both spatially proximate and distal residues)

| PIM (X) | Suppressor Mutant (Y) | ASA (%) | Depth (Å) | Rank-Score[a] | Shortest distance[b] (Å) | Cent-cent distance[c] (Å) |
|---|---|---|---|---|---|---|
| V5F[d] | | 0 | 6.8 | 54 | | |
| | L36M[d,e] | 0 | 7.3 | 83 | 3.9 | 5.5 |
| | A81G[d,e] | 32.4 | 3.9 | 26 | 2.8 | 4.2 |
| V18W | M63T[e] | 0 | 9.3 | 59 | | |
| | | 0.1 | 8.1 | 46 | 4.2 | 5.8 |
| | I90V[e] | 0.1 | 7.4 | 60 | 4.8 | 5.9 |
| V20F | E11R[f] | 0 | 8.6 | 60 | | |
| | | 112.7 | 3.4 | 1 | 18.4 | 22.4 |
| | E11K[f] | 112.7 | 3.4 | 1 | 18.4 | 22.4 |
| L36A | M63L[e] | 0 | 7.3 | 83 | | |
| | | 0.1 | 8.1 | 46 | 3.8 | 6.4 |
| | R10G[f] | 76.6 | 3.6 | 1 | 11.6 | 18.1 |
| | E11P[f] | 112.7 | 3.4 | 1 | 11.7 | 16.8 |
| L83S | | 1.5 | 5.8 | 42 | | |
| | V54L[e] | 0.4 | 5.7 | 28 | 3.9 | 4.5 |

[a]RankScore for residues X or Y estimated from phenotypic screening of single-site saturation mutagenesis library of CcdB and deep sequencing (Adkar, Tripathi et al. 2012)
[b]Shortest distance between residues X and Y
[c]Distance between side chain centroids of residues X and Y
[d]The suppressors (Y) were identified as a triple mutant with the PIM (X) V5F i.e. V5F/L36M/A81G
[e]Suppressor residues spatially proximal to PIM
[f]Suppressor residues distal from the PIMHeavy atoms of the residues are considered for calculating distances using the crystal structure of CcdB, PDB id 3VUB (Loris, Dao-Thi et al. 1999).

TABLE 3

(Relative expression, binding and stabilities of PIMs and their suppressors in the case of CcdB)

| Protein | $K_d$ (nM) determined by FACS | Saturation MFI[a] (surface expression) | Saturation MFI[a] (binding) | $T_m^b$ (° C.) in absence of CcdA | $T_m^b$ (° C.) in presence of CcdA |
|---|---|---|---|---|---|
| WT | 0.3 ± 0.1 | 1280 ± 181 | 14225 ± 1883 | 66.8 ± 1.0 | 78.0 ± 0.1 |
| R10G | 5.3 ± 0.7 | 1676 ± 56 | 13497 ± 90 | 74.8 ± 0.2 | 76.1 ± 0.1 |
| V5F[c] | >120 | 363 ± 7 | 153 ± 7 | d | d |
| V5F/A81G/M63T[c] | 5.6 ± 0.1 | 436 ± 42 | 4572 ± 806 | e | e |
| V18W[c] | >258 | 291 ± 13 | 153 ± 26 | 41.9 ± 0.5 | 64.4 ± 0.5 |
| V18W/M63T[c] | 2.3 ± 0.5 | 407 ± 1 | 1089 ± 112 | 41.8 ± 0.4 | 72.4 |
| V18W/I90V[c] | 67.9 ± 8.3 | 454 ± 37 | 920 ± 202 | d | d |
| V20F[c] | >988 | 667 ± 18 | 264 ± 21 | d | d |
| V20F/E11R[c] | 16.7 ± 0.9 | 577 ± 41 | 1011 ± 513 | d | d |
| L36A | 1.9 ± 1.2 | 316 ± 7 | 2682 | 47.1 ± 0.3 | 70.3 ± 0.7 |
| L36A/M63L | 0.6 | 1106 ± 67 | 10642 ± 23 | 55 ± 0.8 | 75.9 ± 0.1 |
| L36A/R10G | 1.2 ± 0.4 | 867 ± 67 | 12040 ± 1088 | 55.1 ± 0.4 | 64.0 ± 0.4 |
| L83S | 2.1 ± 0.9 | 253 ± 5 | 2175 ± 130 | 46.0 ± 0.6 | 70.3 ± 0.1 |
| L83S/V54L | 0.4 ± 0.3 | 843 ± 21 | 13615 ± 151 | 52.5 ± 0.6 | 74.2 ± 0.3 |

[a]MFI corresponds to Mean Fluorescence Intensity observed from FACS analysis.
[b]Tm corresponds to melting temperature of purified proteins monitored by thermal denaturation (see Materials and Methods) of 4 μM of CcdB (toxin) protein in presence/absence of 20 μM CcdA (antitoxin) peptide (residues 46-72). The presence of ligand, CcdA shifts the unfolding equilibrium towards the folded fraction of CcdB, resulting in an increased Tm than when monitored in its absence.
[c]The proteins have been induced at 20° C. prior to sort and analysis by FACS. The remaining proteins have been induced at 30° C.
[d]Protein could not be purified, and hence $T_m$ was not measured. V5F, V20F, V20F/E11R, V18W/I90V CcdB mutants were unstable and could not be purified due to either low expression and/or inability to bind to CcdA peptide (immobilized to the column for purification) (see Materials and Methods).
[e]The protein was purified but not subjected to thermal denaturation due to difficulty in purifying its PIM. Thus, comparative stability analysis of the pair could not be carried out.
± indicates standard deviation from two independent experiments.

TABLE 4

(Experimentally determined (PIM, Suppressor) pairs for DgkA are spatially close only in the corresponding crystal structure)

| PIM position | Contact partners[a] in X-Ray structure[b] | Contact partners[a] in NMR structure[c] | Experimentally identified (PIM, Suppressor) pairs |
|---|---|---|---|
| V62 | A41, 108, W112 | L102, I103 | (V62Q, A41G) |
| M66 | F31, G35, V38 | A99 | (M66L, V38A) |
|  |  |  | (M66S, G35A) |
| I67 | A100, I103, A104 | F31, E34 | (I67V, I103L) |
|  |  |  | (I67V, A104T) |
| V68 | A100, V101, A104 | F31, G35 | (V68G, A100V) |
| W112 | A41, I44, L58, S61 | — | d |

[a]Inter-helical contact pairs (see Materials and Methods for details)
[b]X-Ray structure of DgkA (PDB id 3ZE5 (Li et al, 2013))
[c]NMR structure of DgkA (PDB id 2KDC (Van Horn et al, 2009))
— No inter-helical contacts
[d]No suppressors for this PIM could be isolated, probably because the large volume change in the PIM (W112V) is difficult to compensate by a single suppressor mutation.

TABLE 5

(Sidechain-sidechain centroid distances and shortest distances between the listed residue pairs for putative differential contacts between DgkA X-ray and NMR structures (experimentally observed (PIM, suppressor) pairs are indicated in bold).

| Differential Contact Residues[a] | | Centroid-centroid Distance (Å)[b] | | Shortest Distance (Å)[c] | |
|---|---|---|---|---|---|
| PIM (X) | (Y) | X-ray | NMR[d] | X-ray | NMR[d] |
| 62 | 41 | 3.8 | 8.4 | 3.6 | 8 |
| 62 | 108 | 4.9 | 11.4 | 4.4 | 10.3 |
| 62 | 112 | 5.8 | 15.8 | 3.1 | 13 |
| 62 | 102 | 14.9 | 6.5 | 14.1 | 5.1 |
| 62 | 103 | 10.9 | 3.9 | 9.2 | 3.5 |
| 66 | 31 | 5.2 | 10.8 | 3.7 | 9.2 |
| 66 | 35 | 4.8 | 10.4 | 3.6 | 8.4 |
| 66 | 38 | 3.8 | 9.5 | 3.5 | 7.8 |
| 66 | 99 | 8.5 | 3.7 | 7.5 | 3.1 |
| 67 | 100 | 5.1 | 10.8 | 4.2 | 10.1 |
| 67 | 103 | 5.4 | 12.4 | 3.6 | 9.8 |
| 67 | 104 | 4.7 | 16.1 | 3.8 | 15 |
| 67[e] | 31[e] | 10.5 | 8 | 8.3 | 5.7 |
| 67 | 34 | 9.9 | 5 | 7.8 | 3 |
| 68 | 100 | 5 | 12.9 | 3.9 | 11.7 |
| 68 | 101 | 5.1 | 13.8 | 3.6 | 12.2 |
| 68 | 104 | 4.1 | 16.6 | 4 | 16.3 |
| 68 | 31 | 11.2 | 6.1 | 9.5 | 4.6 |
| 68 | 35 | 13 | 5.3 | 12.5 | 4.5 |
| 112 | 41 | 5.2 | 10.2 | 3.5 | 8.8 |
| 112 | 44 | 6.9 | 8.4 | 4.1 | 5.7 |
| 112 | 58 | 4.2 | 8.4 | 3.5 | 8.3 |
| 112 | 61 | 5.5 | 15.2 | 3.3 | 13.7 |

[a]Contact present in either X-ray or NMR structure. Contact defined by sidechain-sidechain centroid distance ≤ 7 Å.
[b]Distance between side chain centroids of residues X and Y
[c]Shortest distance between residues X and Y
[d]Closest distance amongst the distances calculated for all 16 poses of the NMR structure
[e]For the residue pair 67-31, the distances in both the X-ray and NMR structures is >7 Å, in the case of the NMR structure, the side chains point towards each other and hence it was shortlisted as an NMR contact.

REFERENCES

Adkar, B. V., A. Tripathi, et al. (2012). Structure 20(2): 371-381.
Anfinsen, C. B. (1973). Science 181(4096): 223-230.
Araya, C. L., D. M. Fowler, et al. (2012). Proc Natl Acad Sci USA 109(42): 16858-16863.
Ashkenazy, H., O. Penn, et al. (2012). Nucleic Acids Res 40(Web Server issue): W580-584.
Baba, T., T. Ara, et al. (2006). Mol Syst Biol 2: 2006 0008.

Bahadur, R. P. and P. Chakrabarti (2009). BMC Struct Biol 9: 76.
Bajaj, K., P. C. Dewan, et al. (2008). Biochemistry 47(49): 12964-12973.
Bank, C., R. T. Hietpas, et al. (2015). Mol Biol Evol 32(1): 229-238.
Bershtein, S., K. Goldin, et al. (2008). J Mol Biol 379(5): 1029-1044.
Bershtein, S., M. Segal, et al. (2006). Nature 444(7121): 929-932.
Bowers, P. M., C. E. Strauss, et al. (2000). J Biomol NMR 18(4): 311-318.
Bowley, D. R., A. F. Labrijn, et al. (2007). Protein engineering, design & selection: PEDS 20(2): 81-90.
Breen, M. S., C. Kemena, et al. (2012). Nature 490(7421): 535-538.
Burger, L. and E. van Nimwegen (2010). PLoS Comput Biol 6(1): e1000633.
Chao, G., W. L. Lau, et al. (2006). Nature protocols 1(2): 755-768.
Cross, T. A., D. T. Murray, et al. (2013). Eur Biophys J 42(10): 731-755.
Dao-Thi, M. H., L. Van Melderen, et al. (2005). J Mol Biol 348(5): 1091-1102.
Das, R., I. Andre, et al. (2009). Proc Natl Acad Sci USA 106(45): 18978-18983.
Das, R. and D. Baker (2008). Annu Rev Biochem 77: 363-382.
De Jonge, N., A. Garcia-Pino, et al. (2009). Mol Cell 35(2): 154-163.
Finn, R. D., J. Clements, et al. (2011). Nucleic Acids Res 39(Web Server issue): W29-37.
Fowler, D. M., C. L. Araya, et al. (2010). Nat Methods 7(9): 741-746.
Garbuzynskiy, S. O., B. S. Melnik, et al. (2005). Proteins-Structure Function and Genetics 60(1): 139-147.
Gibson, D. G., L. Young, et al. (2009). Nat Methods 6(5): 343-345.
Gietz, R. D. and R. H. Schiestl (2007). Nat Protoc 2(1): 31-34.
Gobel, U., C. Sander, et al. (1994). Proteins 18(4): 309-317.
Godzik, A. and C. Sander (1989). Protein Eng 2(8): 589-596.
Guerois, R., J. E. Nielsen, et al. (2002). J Mol Biol 320(2): 369-387.
Guzman, L. M., D. Belin, et al. (1995). J Bacteriol 177(14): 4121-4130.
Halabi, N., O. Rivoire, et al. (2009). Cell 138(4): 774-786.
Haliloglu, T., A. Kolinski, et al. (2003). Biopolymers 70(4): 548-562.
Havel, T. F., G. M. Crippen, et al. (1979). Biopolymers 18(1): 73-81.
Hecht, M. H. and R. T. Sauer (1985). J Mol Biol 186(1): 53-63.
Hopf, T. A., L. J. Colwell, et al. (2012). Cell 149(7): 1607-1621.
Hubbard, S. (1992). Department of Biochemistry and Molecular Biology, University College of London. on the world wide web at wolf bms.umist.ac.uk/naccess).
Jain, P. C. and R. Varadarajan (2014). Anal Biochem 449: 90-98.
Jones, D. T., D. W. Buchan, et al. (2012). Bioinformatics 28(2): 184-190.
Kamisetty, H., S. Ovchinnikov, et al. (2013). Proc Natl Acad Sci USA 110(39): 15674-15679.
Kellogg, E. H., A. Leaver-Fay, et al. (2011). Proteins 79(3): 830-838.
Langley, K. E., M. R. Villarejo, et al. (1975). Proc Natl Acad Sci USA 72(4): 1254-1257.
Li, D., J. A. Lyons, et al. (2013). Nature 497(7450): 521-524.
Li, W., Y. Zhang, et al. (2003). Proteins 53(2): 290-306.
Loris, R., M. H. Dao-Thi, et al. (1999). Journal of molecular biology 285(4): 1667-1677.
Machingo, Q., M. Mazourek, et al. (2001). Curr Genet 39(5-6): 297-304.
Marks, D. S., L. J. Colwell, et al. (2011). PLoS One 6(12): e28766.
McLaughlin, R. N., Jr., F. J. Poelwijk, et al. (2012). Nature 491(7422): 138-142.
Melamed, D., D. L. Young, et al. (2013). RNA 19(11): 1537-1551.
Melamed, D., D. L. Young, et al. (2015). PLoS Genet 11(2): e1004918.
Melero, C., N. Ollikainen, et al. (2014). Proc Natl Acad Sci USA 111(43): 15426-15431.
Morcos, F., A. Pagnani, et al. (2011). Proc Natl Acad Sci USA 108(49): E1293-1301.
Murray, D. T., C. Li, et al. (2014). Biophys J 106(8): 1559-1569.
Niesen, F. H., H. Berglund, et al. (2007). Nat Protoc 2(9): 2212-2221.
Nugent, T. and D. T. Jones (2012). Proc Natl Acad Sci USA 109(24): E1540-1547.
Olson, C. A., N. C. Wu, et al. (2014). Curr Biol 24(22): 2643-2651.
Ovchinnikov, S., H. Kamisetty, et al. (2014). Elife 3: e02030.
Pakula, A. A. and R. T. Sauer (1989). Proteins 5(3): 202-210.
Pande, V. S., I. Baker, et al. (2003). Biopolymers 68(1): 91-109.
Qu, Y., J. T. Guo, et al. (2004). Nucleic Acids Res 32(2): 551-561.
Raetz, C. R. and K. F. Newman (1978). J Biol Chem 253(11): 3882-3887.
Raetz, C. R. and K. F. Newman (1979). J Bacteriol 137(2): 860-868.
Roscoe, B. P., K. M. Thayer, et al. (2013). J Mol Biol 425(8): 1363-1377.
Schreiber, G., A. M. Buckle, et al. (1994). Structure 2(10): 945-951.
Shah, P., D. M. McCandlish, et al. (2015). Proc Natl Acad Sci USA 112(25): E3226-3235.
Shen, M. Y. and A. Sali (2006). Protein Sci 15(11): 2507-2524.
Shen, Y., O. Lange, et al. (2008). Proc Natl Acad Sci USA 105(12): 4685-4690.
Shusta, E. V., M. C. Kieke, et al. (1999). J Mol Biol 292(5): 949-956.
Sideraki, V., W. Huang, et al. (2001). Proc Natl Acad Sci USA 98(1): 283-288.
Sobolev, V., E. Eyal, et al. (2005). Nucleic Acids Res 33(Web Server issue): W39-43.
Sulkowska, J. I., F. Morcos, et al. (2012). Proc Natl Acad Sci USA 109(26): 10340-10345.
Thompson, J. M., N. G. Sgourakis, et al. (2012). Proc Natl Acad Sci USA 109(25): 9875-9880.
Tokuriki, N. and D. S. Tawfik (2009) Nature 459(7247): 668-673.
Tokuriki, N. and D. S. Tawfik (2009). Science 324(5924): 203-207.
Tripathi, A. and R. Varadarajan (2014). Curr Opin Struct Biol 24: 63-71.

Van Horn, W. D., H. J. Kim, et al. (2009). Science 324 (5935): 1726-1729.
Van Horn, W. D. and C. R. Sanders (2012). Annu Rev Biophys 41: 81-101.
Varadarajan, R., H. A. Nagarajaram, et al. (1996). Proc Natl Acad Sci USA 93(24): 13908-13913.
Wellner, A., M. Raitses Gurevich, et al. (2013) PLoS Genet 9(7): e1003665.
Wen, J., X. Chen, et al. (1996). Nat Struct Biol 3(2): 141-148.
Young, M. M., N. Tang, et al. (2000). Proc Natl Acad Sci USA 97(11): 5802-5806.

We claim:

1. A method for identifying functionally interacting amino acid residues in a protein of interest, wherein the method identifies suppressors of single amino acid mutants in the protein of interest, said method comprising:
   (a) obtaining a first library of single mutation variants of said protein of interest, wherein said each variant contains an amino acid substitution at a single residue position, and at least 70% of each possible amino acid substitution at each residue position of said protein of interest is represented in said first library;
   (b) identifying a first subpopulation of variants from the first library, wherein said first subpopulation comprises a population enriched in single amino acid substitution variants, each of which alters the activity of said protein of interest compared to wild-type levels;
   (c) introducing at least five mutations at different residue positions from said first subpopulation singly in to each variant of the first library to obtain a second library of variants;
   (d) identifying a second subpopulation from said second library, comprising variants, each of which has two amino acid substitutions in said protein of interest;
   (e) identifying a third subpopulation, which is a subset of the said second subpopulation of said second library, wherein in each variant of said third subpopulation, the mutation as identified from each variant of said first library suppresses the altered activity of the variant of the first subpopulation,
   wherein the two substituted amino acids in each variant of said third subpopulation are indicative that the substituted amino acid of a variant member of first library is a suppressor of the substituted amino acid of first subpopulation.

2. The method as claimed in claim 1, wherein in each variant of the third subpopulation, the substituted amino acid of a variant member of the first library is a distal suppressor, said distal suppressor is able to suppress the altered activity of more than one variant comprising a single substituted amino acid as identified in the said first subpopulation, wherein the said variants of the first subpopulation have amino acid substitutions in different residue positions, and said amino acid substitutions in different residues do not suppress each other.

3. The method as claimed in claim 1, wherein in each variant of the third subpopulation the substituted amino acid of a variant member of the first library is a proximal suppressor, wherein said proximal suppressor is able to suppress the altered activity of at least one variant comprising a single substituted amino acid as identified in said first subpopulation.

4. The method of claim 3, wherein the method predicts or validates the structure of a protein of interest by generating information of residues in proximity to each other through identification of proximal suppressors.

5. The method of claim 2, wherein the method identifies amino acid residues and residue positions which modulate thermal stability of a protein of interest by identifying distal suppressors which act as stabilizing mutations in the wild-type background.

6. The method as claimed in claim 4, wherein said protein of interest is a single protein, or a multi-protein complex, wherein said protein of interest has amino acid sequence selected from the group consisting of SEQ ID NO: 1, and SEQ ID NO: 2.

7. The method as claimed in claim 5, wherein said protein of interest is a single protein, or a multi-protein complex, wherein said protein of interest has amino acid sequence selected from the group consisting of SEQ ID NO: 1, and SEQ ID NO: 2.

8. The method as claimed in claim 4, wherein said amino acid substitutions are naturally occurring amino acids.

9. The method as claimed in claim 5, wherein said amino acid substitutions are naturally occurring amino acids.

* * * * *